(12) United States Patent
Rutten et al.

(10) Patent No.: US 6,376,736 B1
(45) Date of Patent: Apr. 23, 2002

(54) PRODUCTION OF HIGH PURITY META-XYLENE

(75) Inventors: Philippe W. M. Rutten, Delft; James S. Law, Leidschendam, both of (NL); Douglas S. Hubbell, Sudbury, MA (US)

(73) Assignee: Washington Group International, Inc., Boise, ID (US)

( * ) Notice: Subject to any disclaimer, the term of this patent is extended or adjusted under 35 U.S.C. 154(b) by 0 days.

(21) Appl. No.: 09/701,792

(22) PCT Filed: Jun. 10, 1999

(86) PCT No.: PCT/US99/13015

§ 371 Date: Dec. 1, 2000

§ 102(e) Date: Dec. 1, 2000

(87) PCT Pub. No.: WO99/64381

PCT Pub. Date: Dec. 16, 1999

Related U.S. Application Data
(60) Provisional application No. 60/089,251, filed on Jun. 12, 1998, and provisional application No. 60/118,712, filed on Feb. 5, 1999.

(51) Int. Cl.$^7$ .............................. C07C 7/00; C07C 7/14
(52) U.S. Cl. ...................... 585/815; 585/805; 585/812; 585/813
(58) Field of Search ................................ 585/812, 815, 585/805, 813

(56) References Cited

U.S. PATENT DOCUMENTS

| | | | |
|---|---|---|---|
| 3,277,200 A | 10/1966 | Smith et al. | 260/674 |
| 3,773,846 A | 11/1973 | Berger | 260/674 A |
| 3,798,282 A | 3/1974 | Bemis et al. | 260/674 A |
| 3,825,614 A | 7/1974 | Bemis et al. | 260/674 A |
| 5,811,629 A | 9/1998 | Hubbell et al. | 585/815 |

Primary Examiner—Walter D. Griffin
Assistant Examiner—Tam M. Nguyen
(74) Attorney, Agent, or Firm—David Silverstein; Andover-IP-Law

(57) ABSTRACT

A continuous process for integrated processing of a $C_{8+}$ aromatic hydrocarbon stream is disclosed for recovery of a high purity meta-xylene product in conjunction with efficient separation and recovery of purified para-xylene and, optionally, purified ortho-xylene products.

21 Claims, 11 Drawing Sheets

PRODUCTION OF HIGH PURITY META-XYLENE

This application claims benefit of provisional application Serial No. 60/089,251 filed Jun. 12, 1998, which claims benefit of provisional application serial No. 60/118,712 filed Feb. 5, 1999.

The present invention relates generally to an improved process for the production of high purity meta-xylene as part of an integrated xylene separation and recovery system utilizing an improved arrangement of fractionation, adsorption and crystallization steps.

BACKGROUND OF THE INVENTION

Commonly, para-xylene is commercially produced from C-8+ aromatic streams, usually the C-8+ fraction of reformate from catalytic reformers. The C-8+ aromatics are typically fed to a distillation column, commonly referred to as a xylene splitter, where the ethylbenzene, para-xylene, meta-xylene, and some or virtually all of the ortho-xylene are taken overhead. Ortho-xylene is normally left in the xylene splitter bottoms stream in a significant amount only if a purified ortho-xylene product is to be produced. If it is, then the xylene splitter bottoms stream is typically fed to an ortho-xylene product column where the ortho-xylene is distilled from the C-9+ aromatics.

The xylene splitter overhead stream is then fed to a para-xylene purification (PXP) unit for the recovery and purification of para-xylene product. This PXP unit separates out the para-xylene, typically either by crystallization or by adsorption onto a molecular sieve, utilizing conventional technologies. The para-xylene-depleted stream withdrawn from the PXP unit is then fed normally to an isomerization unit where the meta-xylene and ortho-xylene are partially converted catalytically to para-xylene. Depending on the type of catalyst, the ethylbenzene in this stream is partially converted in the isomerization unit primarily to either benzene or xylenes. After distilling off toluene and lighter compounds, the C-8+ aromatics from the isomerization unit are fed back to the xylene splitter.

If it is desired that meta-xylene be separated out as a purified product in this type of plant, U.S. Pat. No. 3,773,846 (Berger '846), which is incorporated herein by reference, and other patents (described below) have proposed that meta-xylene purification be done between the PXP unit and the isomerization unit. As with para-xylene, meta-xylene can be purified by either crystallization or adsorption. If crystallization is used, however, the purification of the meta-xylene can be hindered by the para/meta and ortho/meta eutectics. Thus, U.S. Pat. Nos. 3,798,282 (Bemis et al.) and U.S. Pat. No. 3,825,614 (Bemis et al.), which are incorporated herein by reference, teach methods for purifying meta-xylene downstream of a para-xylene crystallization unit by crystallization at temperatures below the para/meta eutectic. These patents teach crystallization techniques whereby the para-xylene crystals will be smaller than the meta-xylene crystals, and this allows for some degree of rough separation. After this first separation, the concentrated meta-xylene can be melted and recrystallized in a second stage to produce high-purity meta-xylene. Using adsorption to purify the para-xylene, as taught Berger '846 is probably a more practical commercial approach when meta-xylene is to also subsequently be purified by crystallization because adsorption can reduce the para-xylene concentration in the meta-xylene crystallization unit feed to well below the para/meta eutectic point and, thus, avoid this eutectic problem.

Berger '846 does not, however, efficiently address the issue of avoiding the meta/ortho eutectic which can form during meta-xylene purification by crystallization. In Berger '846, the ortho-xylene removal is accomplished by fractionation, in particular in a "third fractionation zone", located between the adsorption step and the meta-xylene purification step. Also in Berger '846, a "second fractionation zone" is recommended to be located just upstream of the third fractionation zone. This second fractionation zone is used to concentrate the meta-xylene prior to crystallization by distilling away much of the ethylbenzene. This approach is expensive in terms of both capital and operating costs.

A variety of other approaches to the purification of meta-xylene from mixtures of C-8 aromatic hydrocarbons are known in the art. For example, one familiar approach is a liquid/liquid extraction process as taught by U.S. Pat. Nos. 2,528,892; 2,738,372; 2,848,517; 2,848,518; 3,309,414; 3,515,768; and 3,584,068. The liquid/liquid extraction process of these patents is based on the knowledge that boron trifluoride ($BF_3$) and hydrofluoric acid (HF) will form a complex with meta-xylene that is more stable than the corresponding complexes with para- or ortho-xylenes. When mixed xylenes are mixed with limited amounts of $BF_3$ and large amounts of HF, the xylene/$BF_3$/HF complexes form a heavy, acid, liquid phase that separates from a lighter, hydrocarbon, liquid phase. The acid phase has a high percentage of meta-xylene with lesser amounts of para- and ortho-xylenes. Non-aromatic hydrocarbons do not form complexes and thus stay in the hydrocarbon phase. Depending on conditions, ethylbenzene either stays with the light phase or disproportionates to benzene and diethylbenzene, which can also complex with $BF_3$/HF. Through the use of counter-current contacting, the heavy complex can be stripped of nearly all of the non-meta-xylene hydrocarbons and most of the meta-xylene can be extracted from the light hydrocarbon phase. The complex can then be broken, and the meta-xylene separated out. The ortho-xylene and ethylbenzene can be separated from the para-xylene and residual meta-xylene by distillation.

One of the principal disadvantages of this type of liquid/liquid extraction process is that boron trifluoride and hydrofluoric acid are both extremely corrosive and dangerous chemicals. The environmental and safety risks associated with this type of process are so high as to be unacceptable to many companies and countries today. Also, this type of plant is expensive because of the many pieces of equipment and because of the cost of metals needed to withstand the corrosive nature of the chemicals.

Other known exaction-type purification processes use different chemicals but suffer from similar drawbacks. Thus, U.S. Pat. No. 2,830,105 teaches an extraction with phosphorus pentafluoride and hydrofluoric acid; U.S. Pat. No. 3,707,577 uses lithium chloride and aluminum chloride as part of a somewhat more complex extraction process; and, U.S. Pat. No. 2,562,068 employs a double solvent extraction using sulfur dioxide and pentane.

It is also known to purify meta-xylene by selective reaction followed by some type of separation. In U.S. Pat. Nos. 2,889,382 and 3,644,552, meta-xylene is selectively halogenated in the presence of para-xylene. Subsequent processing by distillation, crystallization and/or adsorption can be used to separate the halogenated meta-xylene from other C-8 aromatic hydrocarbons. The halogenation process, however, is not entirely selective for meta-xylene, and the patented processes employ expensive catalysts and/or highly corrosive materials such as molecular chlorine, hydrochloric and nitric acids. U.S. Pat. No. 2,511,711 teaches selectively sulfonating meta-xylene. As with selective halogenation, this process is not entirely selective for meta-xylene and utilizes highly corrosive chemicals. Still a third variety of selective reaction is selective alkylation of meta-xylene with propylene as taught by U.S. Pat. No. 3,539,650. This process also has many disadvantages. First, the alkylation conversion is very low which results in an expensive alkylation unit. Second, there are reaction yield losses not just once but twice. Third, propylene is needed. Fourth, cumene is made, and usually making additional products is not desirable. Fifth, the processing is very complicated and expensive.

Yet another conventional approach to purification of meta-xylene is an extractive distillation process. U.S. Pat. No. 2,763,604 teaches the use of benzonitrile and similar compounds and mixtures as an extractive distillation solvent. Benzonitrile forms loose complexes with aromatics with the strongest effect being with meta-xylene. The addition of the benzonitrile makes the meta/para separation practical with distillation. It also appears that the ethylbenzene from meta/para separation is easier. Because benzonitrile has a significant vapor pressure, however, the products from this type of distillation would probably need to be water washed and the benzonitrile recovered from the wash. In general, processes using solvents that must be made up are not favored because of the added cost and because of concerns about product contamination. Similarly, U.S. Pat. No. 3,089,829 teaches extractive distillation with benzoic acid, and U.S. Pat. No. 3,849,261 teaches extractive distillation with organo-metallic compounds.

Another well-known approach to the purification of meta-xylene is to use crystallization technology without related adsorption treatment. One such process is described in U.S. Pat. No. 2,884,470 which employs three crystallizers in series. The first is an equilibrium crystallizer that crystallizes para-xylene down to a point just above the para/meta eutectic. The second crystallizer is fed the mother liquor from the first crystallizer. This second crystallizer is "super-cooled" in that para-xylene crystals form but meta-xylene crystals do not form because meta-xylene requires more subcooling to initiate crystal formation. Thus, the mother liquor from this second crystallizer is on the meta-xylene side of the meta/para eutectic composition. The third crystallizer crystallizes meta-xylene from the mother liquor from the second one, which is made possible because the crystallizer is seeded with meta-xylene crystals. A similar process is described in U.S. Pat. No. 2,777,888, where first para-xylene is crystallized down to a temperature below the meta/para eutectic, then ortho-xylene is crystallized with the aid of seeding, and then meta-xylene is crystallized with the aid of seeding. Such crystallization processes, which rely on preferential crystallization to avoid eutectic problems, have not been commercialized, perhaps because impurities and/or equipment surfaces in a commercial installation trigger premature crystallization of some system components.

U.S. Pat. No. 3,277,200 teaches a process for co-crystallizing meta-xylene and para-xylene followed by selectively melting the para-xylene crystals to separate them from the meta-xylene. This patent, like several others that are discussed below, takes advantage of the fact that when meta-xylene is crystallized with lesser amounts of para-xylene (i.e., starting with a meta/para mixture with an initial crystallization temperature just above the eutectic point), the para-xylene crystals tend to be smaller. In all of these patents, the para-xylene is recovered by crystallization within the limits of the meta/para eutectic, and then the mother liquor is further crystallized to form both meta and para crystals. In this patent, the resulting slurry is then heated in a controlled way, which preferentially will first melt the smaller crystals, and then before thermal equilibrium is reached, the slurry is quickly filtered. The resulting cake reportedly can be about 95 percent meta-xylene. A second crystallization, which is not discussed in any detail, could achieve a higher meta-xylene purity. This patent is specifically directed to the use of feeds to the meta-xylene crystallization step containing no more than 3 percent of ethylbenzene and no more than 3 percent ortho-xylene. There is no discussion about what happens if ortho-xylene concentration in the feed is high enough to also crystallize ortho-xylene in the crystallization step. By contrast, the present invention avoids the second meta-xylene crystallization, is not limited to low ethylbenzene concentrations, and addresses the issue of ortho-xylene crystallization.

U.S. Pat. No. 3,544,646 teaches another process for co-crystallizing meta-xylene and para-xylene followed by a separation between meta- and para-xylene based on crystal density. According to this patent, the density of para-xylene crystals is 1.006 g/cc, and the density of meta-xylene crystals is 1.030 g/cc. Para-xylene is first recovered by crystallization close to the eutectic point. Then the mother liquor is further crystallized with enough miscible liquid diluent (e.g., freon) so that the liquid phase in the slurry leaving the second crystallizer has a density between the densities of the two types of crystals. By some sort of separator, presumably a bowl-type centrifuge, the two types of crystals are separated. Thus, a meta-rich stream and a para-rich stream are produced, and each can be recrystallized to make high purity products. The crystal density differences are so small, however, that this idea seems impractical in a commercial operation. This approach also requires large amounts of liquid freon that must also be cooled and recovered, and the diluent lowers the temperatures needed for the same meta-xylene recovery.

A patent somewhat similar in concept to the above-mentioned '646 patent is U.S. Pat. No. 3,798,282 which teaches co-crystallizing meta-xylene and para-xylene followed by a separation based on differences in crystal settling rates. This patent teaches that because the meta-xylene crystals produced are relatively large, they will settle faster in the slurry compared with the smaller para-xylene crystals thereby permitting separation. The '282 patent also suggests advantages to removing ortho-xylene from the feed as a bottoms stream from a xylene splitter before carrying out the meta-/para-xylene crystallization on the remaining feed. In the '282 patent, the ortho-xylene is sent to an isomerization step as an overhead stream from an ortho-xylene column, comparable to the treatment of ortho-xylene in some embodiments of the present invention.

The present invention differs from the '282 patent, however, in several critical respects. First, the present invention uses adsorption rather than co-crystallization/crystal settling for para-xylene separation. Second, partially because the adsorption step alters the para/meta eutectic, crystallization units in the present invention are designed differently and are more efficient. Third, the present invention proposes several ways to separate out the ortho-xylene that are different from what is taught by the '282 patent. Fourth, the concept of using a disproportionation unit instead of the isomerization unit to isomerize recycled ortho-xylene is not taught by the '282 patent.

U.S. Pat. No. 3,825,614 describes still another variation on the co-crystallization concept in which meta-xylene and para-xylene are co-crystallized but under operating conditions such that the para-xylene crystallization rate is substantially lower than the meta-xylene crystallization rate. This process is dependent on starting with a relatively low para-xylene concentration of less than 10 percent, preferably less than 8 percent.

The '614 patent describes two ways to get the para-xylene concentration sufficiently low. First, a diluent, such as toluene, butane, naphthenes, carbon dioxide or ethane can be used. Second, some of the eutectic mixture can be crystallized out in a separate crystallizer before doing the nonequilibrium crystallization. The first technique leads to the complications of introducing a third component into these crystallization systems, while the second approach adds another crystallization treatment, which is costly.

Another variety of meta-xylene purification technology utilizes adsorption of para-xylene by itself or in combination with some type of downstream treatment to achieve greater purification of the meta-xylene. U.S. Pat. No. 3,700,744 is representative of the former approach. In this patent, the ethylbenzene is first distilled off and reacted to extinction in a loop through an isomerization unit. Then the ortho-xylene and C9+ aromatics are all fractionated off the bottom of a xylene splitter. Finally, the remaining stream, which is a relatively pure mix of meta- and para-xylene, is fed to a para-xylene adsorption unit where the two xylenes are separated. This approach to meta-xylene purification, however, is impractical and not economically viable for three reasons. First, it requires the fractionation separation of ethylbenzene from para-xylene, which according to the patent requires about 200 trays and a reflux ratio of about 15 resulting in high capital and energy costs. Second, the separation in the xylene splitter is quite difficult because the split between ortho-xylene and meta-xylene must be very complete. Third, if there are nonaromatics in the feed that boil with meta-xylene, then these compounds will end up in the meta-xylene product. Because it will be difficult to keep nearly all nonaromatics, ortho-xylene, and ethylbenzene out of the feed to the adsorption unit, high purity meta-xylene cannot be efficiently produced using this design.

Several patents, such as U.S. Pat. No. 5,382,747, teach processes in which a para-xylene adsorption is combined with downstream processing of the meta-xylene. U.S. Pat. Nos. 3,770,841 and 3,729,523 describe adsorption processes followed by distillation of meta-xylene. In the '841 patent, two adsorption units are used to recover para-xylene and ethylbenzene as separate pure products. The remaining meta-xylene and ortho-xylene are then purified by distillation. Isomerization is used to convert meta- and/or ortho-xylene to para-xylene. U.S. Pat. No. 3,729,523 is essentially the same as the '841 patent except that the para-xylene and ethylbenzene come off the initial adsorption together. The para-xylene is then separated from the ethylbenzene by crystallization. The problem with these approaches is that neatly all of the para-xylene and ethylbenzene must be recovered as purified products from the adsorption step. Any unrecovered para-xylene or ethylbenzene will end up the meta-xylene product. This requires that the upstream adsorption units must operate so as to provide nearly 100 percent product purity and nearly 100 percent recovery which is not practical.

More relevant to the present invention is U.S. Pat. No. 3,773,846 (Berger), previously discussed. This patent describes a meta-xylene purification process combining para-xylene adsorption with subsequent fractionation of the raffinate to decrease the concentration of ortho-xylene or of an ortho-xylene/ethylbenzene mix and a subsequent meta-xylene crystallization. In either case, the fractionation must reduce the ortho-xylene concentration low enough so as to avoid the ortho/meta eutectic in the subsequent meta-xylene crystallization unit. The differences between this patent and the present invention have been addressed above.

All of the foregoing prior art processes for purifying a meta-xylene product as part of an integrated xylene separation and purification operation therefore have various disadvantages and drawbacks. High costs are incurred due to equipment, maintenance and operating expenses in these prior art processes. These and other drawbacks with and limitations of the prior art processes are overcome, in whole or in part, with the improved meta-xylene purification process of this invention.

OBJECTS OF THE INVENTION

Accordingly, a principal object of this invention is to provide an improved process for purifying meta-xylene from a C-8+ aromatic feed stream.

It is a specific object of this invention to provide an efficient and economical approach to preparing high-purity meta-xylene as part of an integrated xylene separation operation.

It is also an object of this invention to provide a process for purifying meta-xylene from a C-8+ aromatic feed which reduces capital and energy costs by minimizing the number of times that ethylbenzene, ortho-xylene and meta-xylene are distilled.

Still another object of this invention is to provide an improved integrated continuous process for treating a C-8+ aromatic feed for separation and recovery of the para-, meta-, and ortho-xylene components thereof utilizing novel, integrated arrangements of xylene distillation, adsorption, crystallization, and isomerization treatment steps.

Other objects and advantages of the present invention will in part be obvious and will in part appear hereinafter. The invention accordingly comprises, but is not limited to, the processes and related apparatus, involving the several steps and the various components, and the relation and order of one or more such steps and components with respect to each of the others, as exemplified by the following description and the accompanying drawings. Various modifications of and variations on the process and apparatus as herein described will be apparent to those skilled in the art, and all such modifications and variations are considered within the scope of the invention.

SUMMARY OF THE INVENTION

In general, this invention comprises a multi-step continuous process for treating a C-8+ aromatic feed stream. As used herein, the term "continuous process" is meant to refer to an overall process wherein there are continuous feeds into and out of the system, including processes involving intermediate semi-batch processing of certain streams within the system. An aromatic feed is fed to a xylene splitter column, which is operated so as to produce an overhead stream typically comprising predominantly para- and meta-xylenes, with lesser amounts of ethylbenzene and ortho-xylene. A significant amount of the ortho-xylene fed to the xylene splitter is taken off in the bottoms stream with nearly all of the C-9+ aromatic compounds and/or is taken off in a side stream from the column. The amount of ortho-xylene allowed to go overhead in the xylene splitter is kept low enough to avoid the crystallization of ortho-xylene in the downstream meta-xylene crystallization unit. The xylene splitter overhead stream is sent to an adsorption step that separates out high-purity para-xylene and leaves a residual stream, which typically would be over 50 percent meta-xylene. This meta-xylene-rich stream is then sent to a crystallization step that separates out high-purity meta-xylene and leaves a mother liquor stream which goes to the isomerization unit. The recovery of para-xylene in the adsorption unit is sufficiently high so as to avoid crystallizing para-xylene in the meta-xylene crystallization step.

Except for ortho-xylene in the xylene splitter bottoms that is further fractionated to produce a purified ortho-xylene product, the rest of the ortho-xylene either in the bottoms or in a side stream is sent to an isomerization step. This "isomerization step" can be in the isomerization unit, which was fed the crystallization unit mother liquor, or a disproportionation unit which also produces equilibrium xylenes. In general, the isomerization step(s) will be operated (by choice of catalyst, temperature, etc.) so as to approach thermodynamic equilibrium among the xylenes. The C-8+ aromatics from each isomerization step are passed back to the xylene splitter for recycle through the process.

Taken individually, some of the component steps of this invention are generally well-known for one or another use in the art of hydrocarbon processing. No previous xylene separation and purification process, however, is believed to have combined and operated these processing steps in the particular ways described in this invention, and no prior art in this field suggests the surprisingly efficient and advantageous results obtained thereby.

DETAILED DESCRIPTION OF PREFERRED EMBODIMENTS

Figure 1:
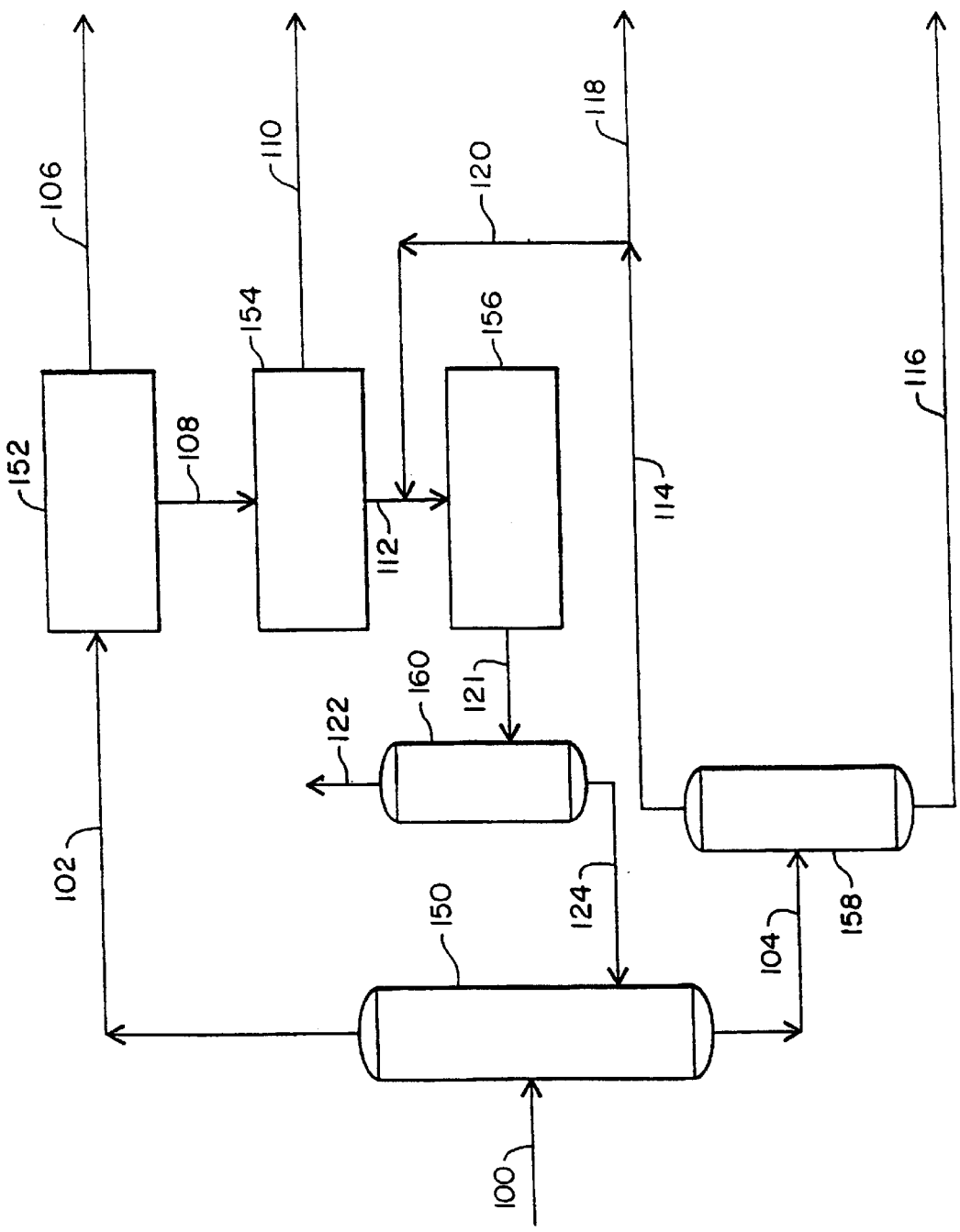
FIG. 1 is a schematic process flow chart illustrating a first embodiment of the present invention.

As shown in FIG. 1, a first embodiment of the present invention, feed stream 100 is fed to a middle or intermediate region of xylene splitter column 150. Feed stream 100 predominantly comprises a mixture of ethylbenzene, para-xylene, meta-xylene, ortho-xylene, and C-9+ aromatic compounds. Xylene splitter 150 is operated such that the xylene splitter overhead stream 102 typically comprises predominantly para- and meta-xylenes, with lesser amounts of ethylbenzene and ortho-xylene. The proportion of ortho-xylene in overhead stream 102 is reduced enough to avoid eutectic problems. At the same time, the xylene splitter bottom stream 104 comprises predominantly ortho-xylene and the C-9+ aromatics.

Xylene splitter overhead stream 102 is fed to adsorption step 152 where typically 95+ percent of the para-xylene is recovered as purified product. The para-xylene-depleted stream from adsorption step 152, referred to herein as raffinate stream 108, is fed directly to a meta-xylene crystallization step 154. As described hereinafter in connection with FIGS. 5–11, in preferred embodiments of this invention meta-xylene crystallization step 154 is carried out by specially designed crystallization processes. It is within the scope of this invention, however, to utilize meta-xylene crystallization processes other than those illustrated by FIGS. 5–11 to carry out meta-xylene crystallization step 154 in FIG. 1. A portion of the meta-xylene in this stream is recovered in this step as high-purity meta-xylene product 110. The remaining C-8 aromatics, which are in the net mother liquor stream 112 coming from crystallization step 154, are fed to the isomerization step 156.

The amount of ortho-xylene removed from the bottom of the xylene splitter and taken overhead in the ortho-xylene recovery column is sufficient to avoid the meta/ortho eutectic in the meta-xylene crystallization step. If the need for purified ortho-xylene product is less than the flowrate of ortho-xylene recovery column distillate (there may be no ortho-xylene product), then the excess ortho-xylene-rich distillate is sent as stream 120 (as hereinafter described) with mother liquor stream 112 to the isomerization step 156.

Alternatively, when purified ortho-xylene is a desired product, it may be advantageous in some cases, especially in cases where meta-xylene production is added to existing para-xylene plants, to have an ortho-xylene recovery column followed by an ortho-xylene product column. This alternative has at least two potential advantages over what is illustrated in FIG. 1. First, with two ortho-xylene columns, the separation in the xylene splitter can be easier because more para- and meta-xylenes can be allowed out the bottoms. Most of these para- and meta-xylenes will be taken overhead in the ortho-xylene recovery column and will be kept out of the ortho-xylene product. Second, if the ortho-xylene product column already exists when meta-xylene production is to be added, then the ortho-xylene recovery column can be added so as to take the added fractionation load and continue utilizing the existing ortho-xylene product column In isomerization step 156, xylenes are reacted catalytically to near thermodynamic equilibrium, and ethylbenzene is partially either dealkylated to benzene or isomerized to xylenes, depending on the catalyst used. After a stream 122 of toluene and lighter components is removed by a fractionation step 160, the isomerized C-8 aromatic stream 124 is recycled to xylene splitter 150.

An important feature of this invention is the surprising and unexpected discovery that, for the typical raffinate streams 108 that are available in commercial aromatics plants with ortho-xylene purification, economical recovery of a high-purity meta-xylene product can be achieved utilizing the process of this invention without the need for first treating the raffinate stream for removal of ethylbenzene and ortho-xylene by expensive fractionation steps according to the teachings of the prior art (e.g., Berger '846).

Compared with the superficially similar process taught by Berger '846, the process of this invention has many advantages. First, whereas the process diagramed in the Berger '846 patent requires two large and expensive fractionation columns, 16 and 19, between the adsorption step and the meta-xylene crystallization step, none of the embodiments of this invention require any intermediate processing of raffinate stream 108 coming from adsorption step 152. In the Berger '846 patent, the separation in the second fractionation zone is essentially between ethylbenzene and meta-xylene with a relatively volatility of 1.066 at 175° C.; and, in the third fractionation zone, the separation is between meta-xylene and ortho-xylene with a relative volatility of 1.134 at 175° C. With a higher relative volatility, a distillation column needs fewer trays and/or less reflux. As relative volatility is reduced towards 1.0, on the other hand, the required number of trays and the reflux flowrate both approach infinity. Thus, the very low relative volatilities in the second and third fractionation zones of Berger '846 require a large number of fractionation stages and high reflux ratios, so that the columns required to make the desired separations necessarily will be very large and costly. By eliminating these two fractionation columns, the complexity of the process is reduced, which makes it much easier to integrate a meta-xylene crystallization step into an existing para-xylene recovery plant, utilizing selective adsorption of para-xylene and isomerization of mixed xylenes. The prior art in this field, however, fails to teach or suggest that it might be possible to successfully practice such a process without one or both of these fractionation columns. Depending on the specifics of an existing para- and ortho-xylene plant, potentially only a single unit (namely the meta-xylene crystallization) needs to be added to an existing plant, and high purity meta-xylene can be produced without materially affecting the existing para- and ortho-xylene production capacities of this system.

Second, the present invention uses less energy. In the Berger '846 patent, the meta-xylene, which is the component with the largest concentration in most of the major streams, must be vaporized nearly three times: in the xylene splitter (reference numeral 2 in Berger '846), in the adsorption unit raffinate column (reference numeral 10 in Berger '846), and, mostly, in the second/third fractionation zones (reference numerals 16 and 19) as shown in the Berger '846 figure. The adsorption unit raffinate column of the present invention (not separately shown in FIGS. 1–4) is a distillation column that distills the raffinate stream from the adsorption unit solvent (or desorbent). In the present invention, by contrast, the meta-xylene is distilled in only the xylene splitter and the raffinate column. Similarly, the ortho-xylene that is not taken off with the C-9+ aromatics in the Berger '846 figure is vaporized more than two times: in the xylene splitter, in the raffinate fractionator, and, partially, in the second fractionation zone. By contrast, in the first embodiment of this invention, this ortho-xylene is split and distilled partly twice, in the xylene splitter and in the raffinate fractionator, and partly only once in the ortho-xylene recovery column. Even though the meta-xylene feed to crystallization is less concentrated in the present invention as compared to that in the Berger '846 patent, the difference in utilities required would be relatively small because of the low total energy requirement by the crystallization unit relative to other parts of the overall process.

The savings in energy realized by the process of this invention is further evidenced by considering the relative volatility in the fractionation of the Berger '846 patent as compared with the relative volatility in the ortho-xylene recovery column of the first embodiment of this invention. In Berger '846, the separation in the third fractionation zone is between meta-xylene and ortho-xylene (relative volatility of 1.134 at 175° C.); whereas, with no ortho-xylene product taken off from the ortho-xylene recovery column, the separation in this column in the first invention embodiment is relatively easy because the separation is between ortho-xylene and meta-ethyltoluene, with a relative volatility of 1.504 at 175° C. The propylbenzenes (cumene and normal-propylbenzene) in the reformate boil between ortho-xylene and the ethyltoluenes, but they can at least partially be taken overhead in the ortho-xylene recovery column when there is no ortho-xylene product because their concentrations in the C-8+ aromatic feed tend to be small and they will be reacted to desirable products in the isomerization unit.

Third, by not removing the ethylbenzene in a second fractionation zone, the present invention avoids creating a problem with the ortho- and meta-xylene eutectic in the operating range envisaged. With some ortho-xylene net production, the composition of a typical adsorption unit raffinate stream (for example, as in the illustrative embodiment in the Berger '846 patent) allows for significant recovery of meta-xylene by crystallization before the ortho-/meta-xylene eutectic is reached. In the illustrative embodiment of the Berger '846 process, however, the loss of meta-xylene with the ethylbenzene overhead stream in the second fractionation column ortho-xylene will crystallize at a warmer temperature than meta-xylene. As a result, the recovery of meta-xylene in the crystallization unit is not possible because of the shifted eutectic limit. Because of this problem, the Berger '846 process must also add the third fractionation step to achieve significant production rates of meta-xylene from the crystallization unit Nevertheless, these rates are still well below those achievable with the present invention.

Finally, by removing more of the ortho-xylene upstream of the adsorption unit, the adsorption unit is less expensive to install and operate. Because adsorption unit feed flow is smaller and the para-xylene in the feed is more concentrated, the amount of molecular sieve can be reduced, and the raffinate column in the adsorption unit can be smaller and use less energy.

Figure 2:
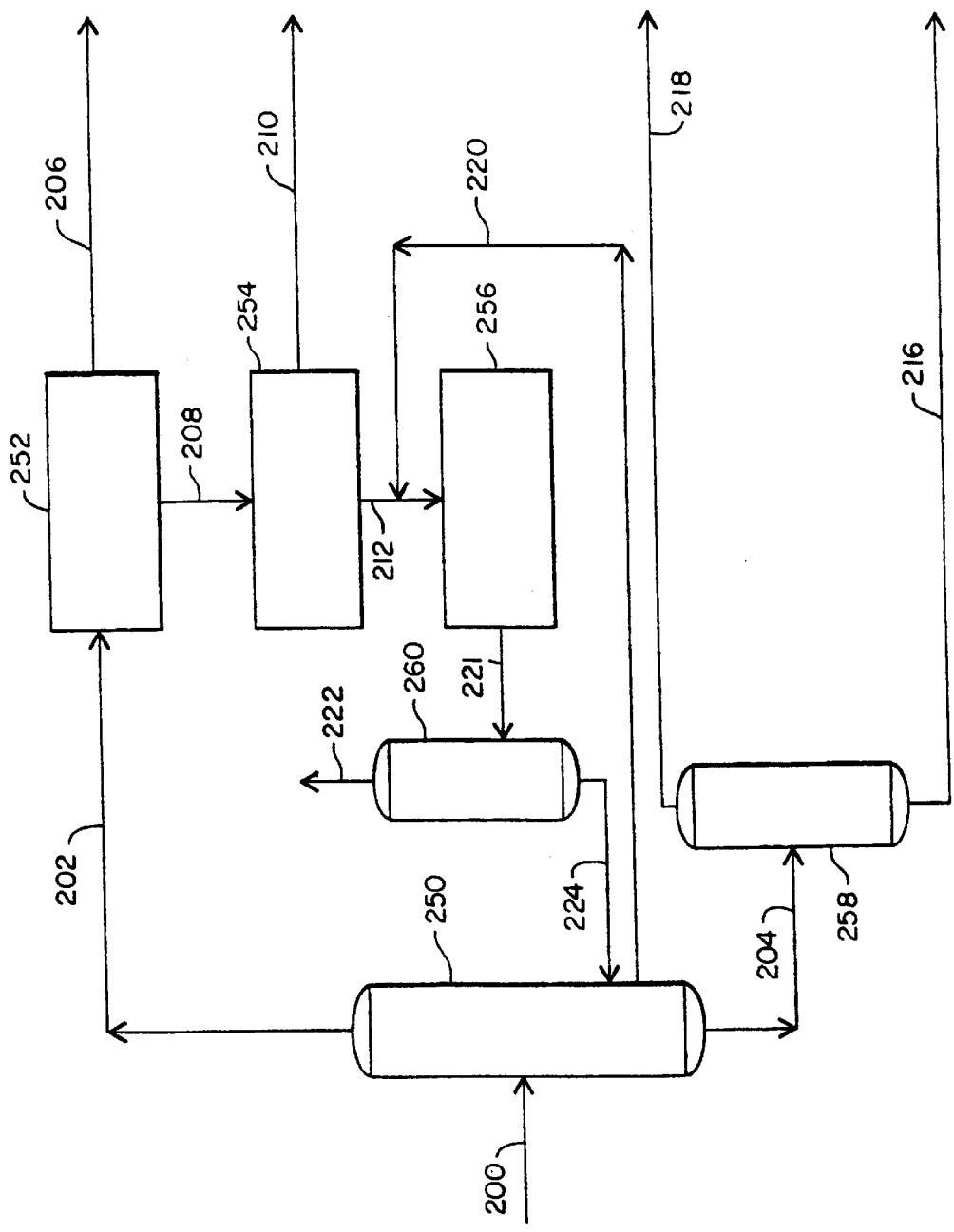
FIG. 2 is a schematic process flow chart illustrating a second embodiment of the present invention.

As shown in FIG. 2, a second embodiment of the present invention, feed stream 200 is fed to a first intermediate region of xylene splitter column 250. Feed stream 200 will predominantly comprise a mixture of ethylbenzene, para-xylene, meta-xylene, ortho-xylene, and C-9+ aromatic compounds. Xylene splitter 250 is operated such that the xylene splitter overhead stream 202 typically comprises predominantly para- and meta-xylenes, with lesser amounts of ethylbenzene and ortho-xylene.

As shown in FIG. 2, xylene splitter 250 is designed and operated so as to permit the withdrawal of an ortho-xylene-rich side stream 220 from a second intermediate region of column 250 below the first intermediate region where feed 200 is added. This side stream 220 is totally sent to the isomerization unit for partial conversion of the ortho-xylene to meta-and para-xylenes. In general, for similar mass flow rates, splitter 250 will be a larger column, with more trays, as compared with column 150 in the embodiment of FIG. 1. On the other hand, with this embodiment, it is possible to eliminate the separate ortho-xylene recovery column 158 in FIG. 1. Instead, the withdrawn ortho-xylene-rich side stream 220 may be sent directly to the isomerization step 256. Bottoms stream 204 coming from xylene splitter 250 will thus comprise predominantly C-9+ aromatic compounds, which are withdrawn from the process. If a purified ortho-xylene product is needed, then ortho-xylene would be drawn off the bottom of the xylene splitter with the C-9+ compounds and sent to an ortho-xylene product column (as shown in FIG. 2) for separation from the C-9+ compounds. Except for the operation of the xylene splitter and the elimination of a separate ortho-xylene recovery column, all other elements and flow streams in FIG. 2 generally correspond to similarly numbered elements or flow streams shown and described in connection with FIG. 1 (e.g., adsorption step 252 in FIG. 2 corresponds to adsorption step 152 in FIG. 1, and meta-xylene crystallization step 254 in FIG. 2 corresponds to meta-xylene crystallization step 154 in FIG. 1).

Figure 3:
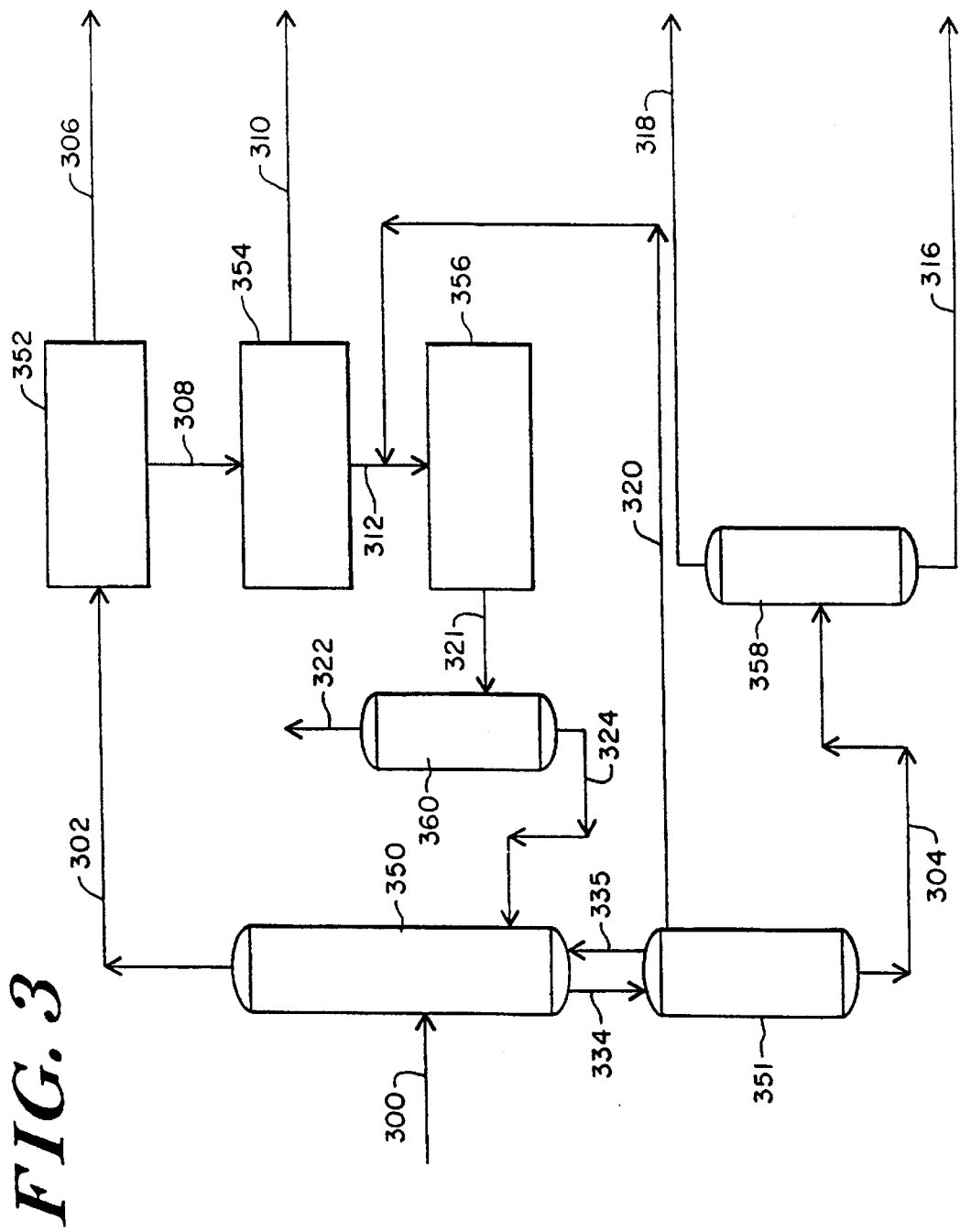
FIG. 3 is a schematic process flow chart illustrating a third embodiment of the present invention.

FIG. 3 illustrates still another embodiment of the present invention, essentially a variation on the process illustrated by FIG. 2. The only significant difference between the FIG. 3 and FIG. 2 embodiments is that in FIG. 3 the xylene splitter step uses two columns, the second column 351 functioning as essentially a physical extension of the first column 350. All other elements and flow streams in FIG. 3 generally correspond to similarly numbered elements or flow streams shown and described in connection with FIG. 2. The liquid bottoms stream 334 from xylene splitter column 350 feeds the top of the extension column 351, and overhead vapor stream 335 from column 351 feeds the bottom of column 350. In FIG. 3, the ortho-xylene-rich stream 320 is shown coming from the upper part of the extension column 351, and the feeds 300 and 324 are shown feeding the xylene splitter 350; however, the split between the two columns is a matter for case-to-case optimization, and the connections of streams 320,350, and 351 may be on either of the two columns. In any case, the side stream 320 should be withdrawn from below the two feed locations.

Similar to FIG. 2, the FIG. 3 embodiment normally utilizes only a single reboiler on extension column 351 and only a single reflux-producing condenser condensing vapor from the top of column 350. The embodiment of FIG. 3 is particularly useful commercially where an existing para-xylene production operation is to be refitted to operate in accordance with this invention to also produce a high-purity meta-xylene product. The embodiments of FIGS. 2 and 3 can both have energy efficiency advantages over the FIG. 1 embodiment because the same reboiler heat can be used for both the separation of the para/meta stream for feeding the adsorption unit and the separation of an ortho-xylene-rich stream for sending directly to the isomerization step.

Figure 4:
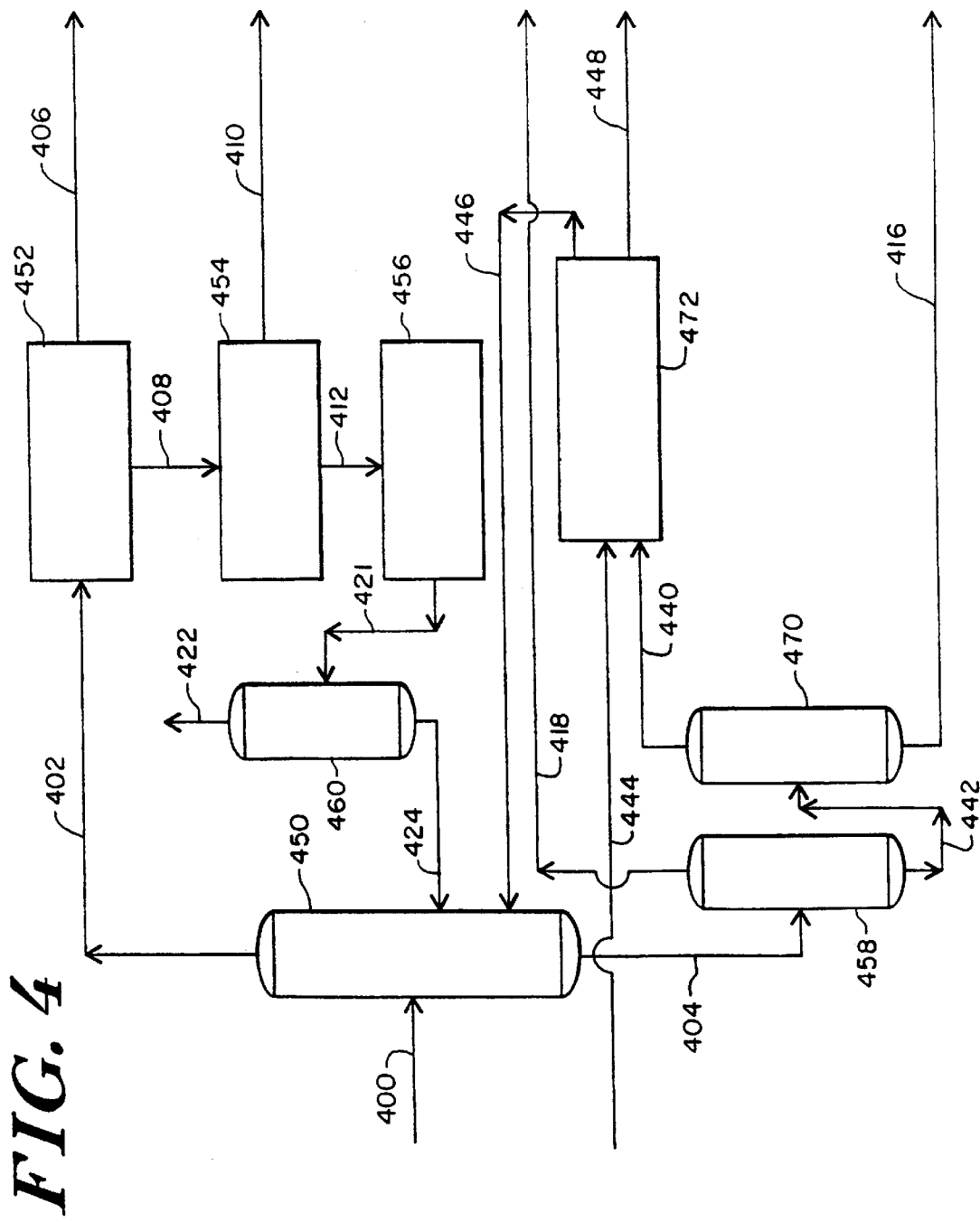
FIG. 4 is a schematic process flow chart illustrating a fourth embodiment of the present invention.

Still a fourth embodiment of the present invention is illustrated by FIG. 4. FIG. 4 will be seen to be yet another variation of FIG. 1. In FIG. 4, however, the ortho-xylene recovery column 158 (in FIG. 1) is replaced by an $A_9/A_{10}$ splitter column 470 operated so as to separate ortho-xylene together with C-9 aromatics as an overhead stream 440, from the C-10+ aromatics which are withdrawn as bottoms stream 416. This variation of the invention is also designed to operate in conjunction with a disproportionation step 472. Disproportionation technology is well known in the art and can be used to achieve equilibration among a mixture of different xylene isomers.

If a purified ortho-xylene product is to be produced with this embodiment, then an ortho-xylene product column 458 can, as in the FIG. 2 embodiment, be fed the xylene splitter bottoms. In this embodiment, the ortho-xylene product column bottoms 442 would feed the $A_9/A_{10}$ splitter 470. As with the FIG. 1 embodiment, the production of a purified ortho-xylene product may require a tighter specification of para- and meta-xylenes in the xylene splitter bottoms than would be required otherwise.

As shown in FIG. 4, a toluene stream 444, preferably from a source in an integrated aromatics plant operation, is optionally fed together with the ortho-xylene and C-9 aromatic overhead stream 440 from splitter 470 to the disproportionation step 472. In the disproportionation step, in the presence of a suitable catalyst, C-9 aromatics plus the optionally fed toluene react to produce benzene and an equilibrium mixture of xylenes and some ethylbenzene. The ortho-xylene fed to the disproportionation step via overhead stream 440 also equilibrates to form an equilibrium mixture of xylenes. After removal of lighter components, the equilibrium mixture of xylenes can then be directly recycled as feed stream 446 to xylene splitter 450, and the benzene stream 448 is separately withdrawn. Except for the $A_9/A_{10}$ splitter column 470 and the disproportionation step 472, as described above, all other elements and flow streams in FIG. 4 generally correspond to similarly numbered elements or flow streams shown and described in connection with FIG. 1. If the disproportionation process can also operate with feed containing C-10 aromatics as well as C-9 and lighter aromatics, then this embodiment is the same except that the $A_9/A_{10}$ splitter 470 would be operated as a $A_{10}/A_{11}$ splitter, and C-11+ aromatics would be withdrawn in bottoms stream 416.

In comparison with prior art processes, particularly the Berger '846 patent, the several embodiments of this invention have numerous advantages. Thus, there are at least five reasons why the embodiment of FIG. 1 of the present invention is an improvement relative to Berger '846. First, if ortho-xylene is to be produced as a purified product, which is often the case, then meta-xylene production can be added to para-xylene plant design without adding distillation columns. By contrast, Berger '846 teaches the use of a third fractionation column or zone.

Second, the feed flows to the second fractionation zone in the process of Berger '846 can be two to ten times larger than the feed to the ortho-xylene recovery column of FIG. 1 of the present invention. Thus, the ortho-xylene recovery column can be smaller and use less energy than the second and third fractionation zones of Berger '846, which saves both initial investment and operating costs. This difference can be explained in the following way. In the Berger '846 invention, the second and third fractionation zones must handle not only all of the ortho-xylene on its way to the isomerization step but also all of the meta-xylene and ethylbenzene, and most of this large flow is distilled. In contrast, the ortho-xylene recover column of FIG. 1 of this invention handles only part of the ortho-xylene and relatively minimal proportions of the other C-8 aromatics.

Third, the separation in the ortho-xylene recovery column is easier, relative to the third fractionation zone in Berger '846, which again saves investment and/or operating cost. In Berger '846, the separation in the third fractionation zone is between meta-xylene and ortho-xylene (relative volatility of 1.134 at 175° C.) whereas the separation in the ortho-xylene recovery column in the FIG. 1 embodiment of the present invention is between ortho-xylene and meta-ethyltoluene (relative volatility of 1.504 at 175° C.) when a purified ortho-xylene product is not being produced. The propylbenzenes (cumene and normal-propylbenzene) in the reformate boil between ortho-xylene and the ethyltoluenes. If the ortho-xylene recovery column is not used to produce ortho-xylene product, then the propylbenzenes can at least partially be taken overhead in the ortho-xylene recovery column because their concentrations in the reformate tend to be small and they will be reacted to desirable products in the isomerization unit.

Fourth, when there is no purified ortho-xylene product, the xylene splitter can potentially be smaller and use less energy relative to the rate and volume of the aromatic feed. In Berger '846, all of the ortho-xylene that is to be isomerized must be vaporized and taken overhead in the xylene splitter, and the separation is between ortho-xylene and cumene (relative volatility 1.217 at 175° C.). In the present invention, more of the ortho-xylene is in the bottoms of the column, and the separation is primarily between meta-xylene and cumene (relative volatility of 1.381 at 175° C.).

Finally, by removing more of the ortho-xylene upstream of the adsorption unit, the adsorption unit can be made smaller and, therefore, less expensive. Because adsorption unit feed flow is smaller and the para-xylene in the feed is more concentrated, the amount of molecular sieve can be reduced, and the raffinate column in the adsorption unit can be smaller and use less energy.

There are also at least four advantages that the embodiments of FIGS. 2 and 3 of this invention have relative to Berger '846. First, if the xylene splitter extension is added to a typical para-xylene plant, then little or no additional energy input is required for the xylene splitter for the added separation of the ortho-xylene-rich stream. In Berger '846, the second and third fractionation zones must be added and must be large enough to handle not only all of the ortho-xylene on its way to the isomerization step but also all of the meta-xylene and ethylbenzene. Furthermore, most of the feed to the second fractionation zone is distilled. The differences in investment and operating costs are therefore substantial.

Second, the separation in the new column is easier, which again saves investment and/or operating cost. In Berger '846, the separation in the third fractionation zone is between meta-xylene and ortho-xylene (relative volatility of 1.134 at 175° C.) whereas the separation in the xylene splitter extension in the FIG. 3 embodiment of the present invention is between ortho-xylene and meta-ethyltoluene (relative volatility of 1.504 at 175° C.). The propylbenzenes (cumene and normal-propylbenzene) in the reformate can at least partially be taken overhead in the xylene splitter extension column because their concentrations in the reformate tend to be relatively small and they will be reacted away in the isomerization unit.

Third, the xylene splitter in FIG. 3, not including the extension column, (or the xylene splitter above the side stream take-off point in FIG. 2) can potentially be smaller. In Berger '846, all of the ortho-xylene that is to be isomerized must be vaporized and taken overhead in the xylene splitter, and the separation is between ortho-xylene and cumene (relative volatility 1.217 at 175° C.). By contrast, in the present invention, a significantly larger proportion of the ortho-xylene is taken out the bottom of the xylene splitter column, with the result that the subsequent required separation becomes the easier one of separating meta-xylene from cumene (relative volatility of 1.381 at 175° C.).

Finally, by removing more of the ortho-xylene upstream of the adsorption unit, the adsorption unit can be made smaller and, therefore, less expensive. Because the adsorption unit feed flow is smaller and the para-xylene in the feed is more concentrated, the amount of molecular sieve can be reduced, and the raffinate column in the adsorption unit can be smaller and use less energy.

Futhermore, there are also at least five advantages that the embodiments of FIG. 4 of this invention has relative to Berger '846. First, the ortho-xylene rerouting does not necessarily require an additional column, unlike the requirement for at least the third fractionation zone in Berger '846. With a disproportionation unit in the design, the $A_9/A_{10}$ splitter is needed anyway; however, the feed and distillate of this column will be larger in this case.

Second, the feed flows to the second fractionation zone in the processes of Berger '846 are several times larger than the added flow, i.e., the ortho-xylene, to the $A_9/A_{10}$ splitter in this embodiment of the present invention. Thus, the added capacity of the $A_9/A_{10}$ splitter can be made smaller and/or use less energy than the second and third fractionation zones of Berger '846. This difference can be explained in the following way. In Berger '846, the second and third fractionation zones must handle not only all of the ortho-xylene on its way to the isomerization step but also all of the meta-xylene and the ethylbenzene, and most of this relatively large liquid flow must be distilled. In contrast, the $A_9/A_{10}$ splitter column handles only part of the total ortho-xylene to be isomerized in addition to the C-9+ aromatics and relatively minimal proportions of the other C-8 aromatics.

Third, the separation in the $A_9/A_{10}$ splitter is easier than that which occurs in the third fractionation zone of Berger '846, which again saves investment and/or operating cost. In Berger '846, the separation in the third fractionation zone is between meta-xylene and ortho-xylene (relative volatility of 1.134 at 175° C.) whereas the separation in the $A_9/A_{10}$ splitter, which is between 1,2,3-trimethylbenzene and diethylbenzenes (relative volatility of about 1.208 at 175° C.), is not significantly impacted by the presence of the relatively-volatile ortho-xylene.

Fourth, when there is no purified ortho-xylene product, the xylene splitter can potentially be smaller and use less energy relative to the rate and volume of the aromatic feed. In Berger '846, all of the ortho-xylene that is to be isomerized must be vaporized and taken overhead in the xylene splitter, and the separation is between ortho-xylene and cumene (relative volatility 1.217 at 175° C.). With the $A_9/A_{10}$ splitter utilized as described for this embodiment of the present invention, part of the ortho-xylene is taken out the bottom of the xylene splitter, and the separation in the xylene splitter is more between meta-xylene and cumene (relative volatility of 1.381 at 175° C.).

Finally, by removing more of the ortho-xylene upstream of the adsorption unit, the adsorption unit is less expensive because its feed flow is smaller and the para-xylene in the feed is more concentrated. The amount of molecular sieve can thus be reduced, and the raffinate column in the adsorption unit can be smaller and use less energy.

In one set of preferred embodiments of this invention, the meta-xylene crystallization step (reference numerals 154, 254, 354 and 454 respectively in FIGS. 1–4) is carried out by specially designed crystallization processes. More particularly, this set of preferred meta-xylene crystallization processes of this invention generally comprise a final product separator, a final product separator feed section which may comprise a crystallization stage, and a total of at least two crystallization stages operating with different slurry outlet temperatures. The final product separator can be a system based on a wash column (for example, as described in U.S. Pat. Nos. 4,332,599; 4,491,462; and 4,475,355), a centrifuge, a filter, or some other solid-liquid separator. Warm temperatures to the final product separator usually promote high product purity and high separation equipment capacity. The meta-xylene product is entirely separated from a crystal-liquid slurry by one or more final product separators. The final product separator feed section slurry being fed to the final product separator should have a temperature in the range of about –51° C. to –68° C. The rest of the process is set up to economically provide this desired slurry feed to the final product separator, which in various embodiments can be systems based on a wash column, centrifuge, filter, or some other solid-liquid separator. In a preferred embodiment, the final product separator is a packed-bed wash column system.

The meta-xylene processes of this set of embodiments of this invention have one or more crystallization stages. A crystallization stage in accordance with this invention can comprise one of several different designs. One useful crystallization stage design is based on the use of scraped-surface double-pipe heat exchangers with the process slurry formed inside the inner pipe and cooling provided between the pipes. This cooling can be provided by boiling refrigerant or a circulating fluid which carries heat from the scraped-surface heat exchangers to the refrigeration system. These heat exchangers can operate on a once through basis or with recirculation to increase velocities for better heat transfer to the slurry. If there is recirculation, then the main flow should go from a vessel to a pump to the exchanger crystallizers and back to the same vessel. This vessel provides cooling for the feed to the crystallizer stage, holdup for stabilizing the process, and also residence time for crystal growth. The net slurry product can be taken from the circulation either before or after the exchanger crystallizers. The net slurry product can either go to the next part of the process directly or through another vessel for additional crystal growth.

A second design for a crystallization stage is to use a vertical scraped-surface jacketed vessel. The process slurry is created inside the vessel, and the vessel jacket has either boiling refrigerant or circulating heat transfer fluid. If required for capacity, there may be multiple crystallizers in parallel.

A third design for a crystallization stage is to operate two or more vessel crystallizers in series. Each crystallizer is referred to as a step, with the warmest crystallizer called the first step. In this design, slurry from the warmest crystallizer is the crystal product of the stage. The slurry from each of the other crystallizers is fed to the next warmest. The slurry is taken off the bottom of each crystallizer. The liquid feeds to the stage are fed to the warmest crystallizer. Filtrate from each crystallizer is separated by gravity in the top section of the crystallizer. In the case of the coldest crystallizer, the filtrate is drawn off as the net filtrate from the stage. The filtrate from each of the other crystallizers in the stage is decanted off and fed to the next coldest crystallizer. In this way, the liquid streams and slurry streams between crystallizers flow countercurrently.

Still a fourth design for a crystallization stage is to use exchanger systems, as described for the first crystallization stage type described above, in series, in place of vessel-type crystallizers in the arrangement in the third design. The filtrate from each step of the stage is drawn off the top of one of the vessels in the step.

A fifth design for a crystallization stage is to use vessel-type crystallizers in series where there is no crystal/liquid separation in the crystallizers, the slurry product of the stage is from the coldest crystallizer, and the slurry from each of the warmer crystallizers flows to the next coldest crystallizer. The first (coldest) stage of the process described in U.S. Pat. No. 3,177,265 is of this type.

A sixth design for a crystallization stage is to use exchanger systems, as described for the first crystallizer stage given above, in series, in place of vessel-type crystallizers in the arrangement given in the fifth design.

The slurry feed to the final product separator comes from the final product separator feed section, which can either be a drum with pump(s) and agitation or a crystallization stage. If the concentration of meta-xylene in the feed is equal to or less than the equilibrium concentration of meta-xylene in the liquid phase of the slurry feeding the final product separator, then this section should be a drum system. If the concentration of meta-xylene in the feed is significantly higher than in the slurry liquid phase, then it may be advantageous to have the final product separator fed from a crystallization stage. In this latter case, the feed is at least partially fed to this stage for fractional crystallization. This crystallization stage is referred to as the "hot" crystallization stage because it operates at a higher temperature than other crystallization stage(s). The final product separator feed section may be fed crystals from other parts of the process, fresh feed in some cases, and recycle filtrate from the final product separator for control of the solids concentration in the feed to the final product separator.

Upstream of the final product separator feed section is in most embodiments the warm crystallization stage which may be in combination with a crystal/liquid separation system, which, for example, may be based on a centrifuge, filter, or other separation devices. This warm stage is fed fresh feed if it is not all fed to the final product separator feed section, part of the recycle filtrate from the final product separator, and possibly crystal slurry or cake from a cold crystallization stage. From this warm-stage crystallization stage or its associated separation system, the crystals are fed to the final product separator feed section, some liquid may be recycled back to the warm crystallization stage for controlling the solids concentration, and the net liquid from the stage either is the net mother liquor of the process or is the feed to the cold crystallizer stage.

If there is a cold crystallization stage, it is fed directly or indirectly the net filtrate from the warm stage. It is not necessary to install this cold stage if the recovery is adequate without it. The cold stage can operate with or without a dedicated slurry separation device, such as a centrifuge or filter. With a separation device, the crystal cake is sent to the warm stage or the final product separator feed section, and part of the filtrate from the device is the net mother liquor of the process. Without the separation device, the crystallization stage must have the capability to decant off the net process mother liquor, and the slurry is sent to the warm crystallization stage. Appropriate heat exchangers can be added to recover cold from the product meta-xylene and net mother liquor, as well as to cool the feed.

In a preferred embodiment of this invention, a packed-bed wash column system is used for the final separation of meta-xylene crystals from the slurry. In one embodiment of the packed-bed wash column, the slurry is fed to the bottom of the column. The filtrate is removed from the bottom, while the purified crystals are transported internally to the top of the column. The crystals form a packed bed and are scraped off the top of the bed into the top head of the wash column, where they are reslurried with pure meta-xylene liquid. The slurry flows from the top head, and the crystals are melted in a heat exchanger. Part of the melt is taken off as the net product, and the rest is recirculated back to the top head to reslurry the crystals and to provide liquid to reflux the wash column. The reflux is essentially all recrystallized within the wash column when the crystals are heated. Packed-bed wash columns, which are especially well suited for use in combination with the crystallization process of this invention, are described in U.S. Pat. Nos. 4,316,368; 4,332,599; 4,491,462; 4,475,355; 4,705,624; 4,787,985; and 5,062,862, which patents are incorporated herein by reference.

FIGS. 5–11 illustrate several specially designed embodiments of the meta-xylene crystallization technology of this invention, each adapting and optimizing the general principles discussed above to suit particular plant conditions, feed stream purities, and other process parameters. In the following descriptions of these figures the final product separator is a packed-bed wash column system, but it will be understood that other types of separators, such as centrifuges, can be substituted for at least some applications.

In general, the meta-xylene crystallization processes of FIGS. 5–11 comprise efficient designs for the final purification of meta-xylene from a feed stream with meta-xylene in the concentration range of about 45 to 85 percent to obtain a final meta-xylene product with a purity of about 99 percent or higher. In general, each of the meta-xylene crystallization processes of FIGS. 5–11 is also designed to be carried out with essentially no external heat input to the process, except for the heat required to melt the final product, so as to minimize refrigeration usage. It will be understood by those skilled in the art that a certain very small amount of heat input from the environment and the machinery is unavoidable. Such minimal, unavoidable heat input is meant to be consistent with the terminology "substantially no heat input."

Furthermore, for certain of the specially designed meta-xylene crystallization processes, as described below, a certain amount of internal heat transfer, for example by means of heat exchange among process streams at different temperatures, may be used for thermal efficiency and to adjust temperatures of various internal streams for optimum performance. Such internal heat transfer is considered distinct from intentional heat input from external sources, such as steam from boilers, intended specifically for partial or complete crystal melting at one or more intermediate stages of the crystallization process. The specially designed meta-xylene crystallization processes of this invention, however, are intended to be carried out so as to realize a minimum of net melting of crystals at intermediate stages of the crystallization process and prior to final product purification.

Thus, the terminology "substantially no heat input" is intended to exclude heat input from external sources intended for intermediate crystal melting, but is not meant to exclude relatively small amounts of crystal melting which may incidentally result from transferring crystals or slurries among the various crystallizers, separators and other process steps or adjusting slurry stream temperatures by internal heat exchange among process streams.

Figure 5:
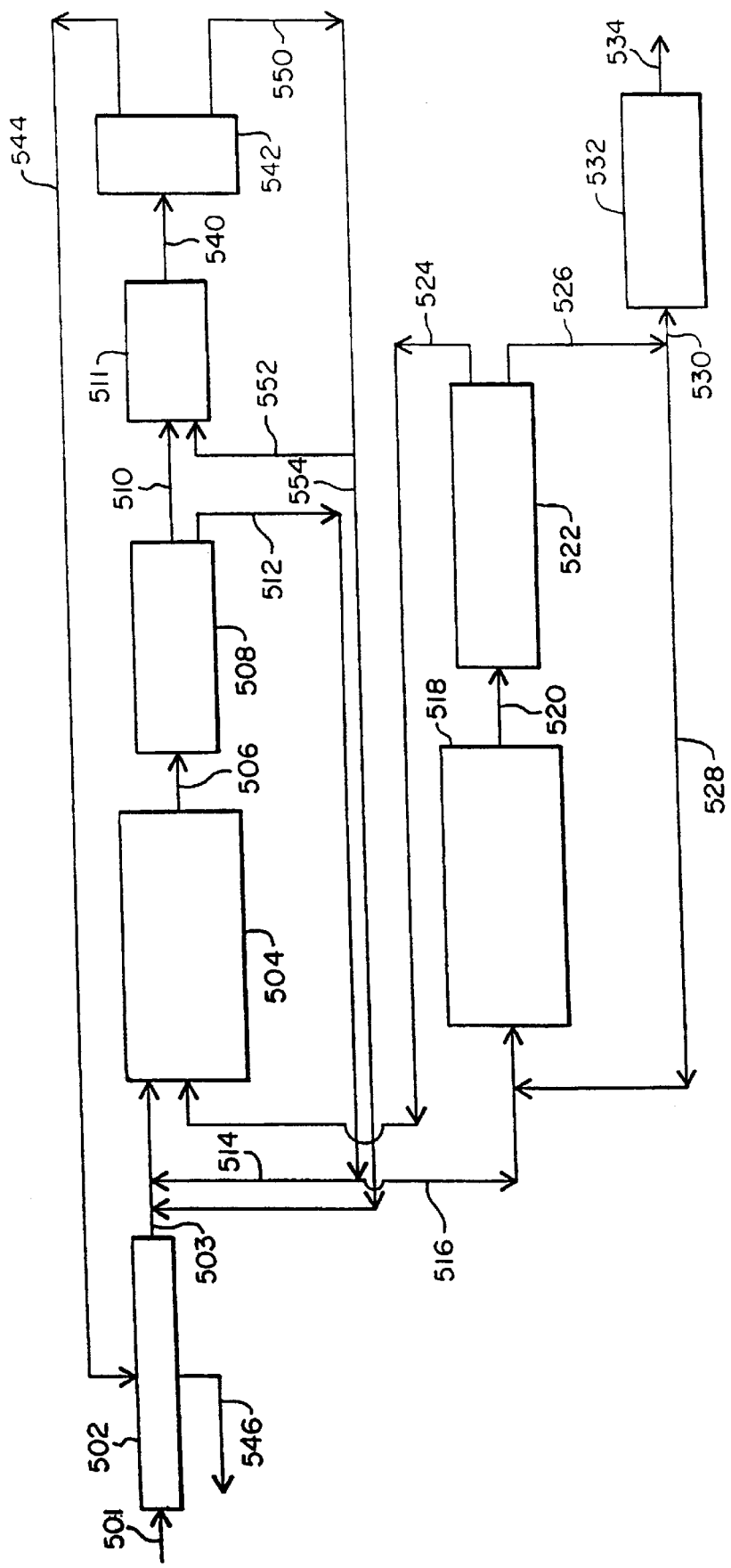
FIG. 5 is a process flow diagram illustrating an embodiment of the meta-xylene crystallization process of this invention wherein purified meta-xylene is produced by a two-stage crystallization process where the final product separator feed section is based on a drum, referred to as a slurry drum, and there is a cold crystallization stage with a cold-stage crystal/liquid separator, which sends crystals to the warm crystallization stage, which is followed by another crystal/liquid separator, which sends its crystals to the slurry drum.

FIG. 5 is a schematic of a meta-xylene crystallization process according to the present invention in which the meta-xylene-rich residual stream feed is cooled and is then combined with recycled filtrate streams from the packed-bed wash column and optionally the warm centrifuge. The amount of filtrate recycled from the warm centrifuge is used to control the concentration of crystals in the warm crystallization stage. The combined stream is then fed with the crystals from the cold centrifuge to the warm crystallization stage.

The warm crystallization stage cools the combined stream and increases the crystal concentration. The resulting slurry is then fed to the warm centrifuge. Part of the centrifuge filtrate is recycled as required to the warm crystallization stage, as previously described, while the remaining filtrate becomes the feed to the cold crystallization stage. The crystals from the warm centrifuge drop into a slurry drum. In the slurry drum, the crystals from the warm centrifuge are mixed with recycled filtrate from the wash column. The amount of filtrate recycled is set to control the concentration of crystals leaving the slurry drum. To warm the crystals, a small amount of heat may be added to the slurry drum or, alternatively, heat may be added to one or more of the feed streams to the slurry drum, for example by passing the recycled filtrate through a heat exchanger.

From the slurry drum, the slurry stream is pumped to the wash column. In the wash column, the crystals are separated from the filtrate and washed of impurities. The filtrate is recycled, with a portion going to the slurry drum and the rest being sent to the warm crystallization stage. The crystals from the wash column are melted in the wash column system, heated against the feed, and pumped to storage as the purified meta-xylene product.

The net filtrate from the warm centrifuge is combined with recycled filtrate from the cold centrifuge and fed to the cold crystallization stage, where cooling and crystallization occur. The slurry from the cold crystallization stage goes to the cold centrifuge. The crystals from the cold centrifuge are sent back to the warm crystallization stage. Part of the filtrate from the cold centrifuge may be recycled to the cold crystallization stage for crystal concentration control. The remaining filtrate is warmed up in a heat exchanger and withdrawn from the meta-xylene crystallization process as a xylene-depleted net mother liquor stream, at least a portion of which is sent to the isomerization step.

Referring now specifically to FIG. 5, the residual stream 501 from the adsorption treatment, as previously described, is passed through heat exchanger 502 and then fed as stream 503 to a first (warm) crystallization stage 504 operated with an outlet temperature of about −60° C. to −80° C., depending on the feed purity. Slurry 506 from crystallizer 504 is fed to a first (warm) centrifuge 508 which separates a meta-xylene crystal product stream 510 from a mother liquor stream 512.

Crystal stream 510 is fed to a slurry drum 511 operated in the range of −51° C. to −68° C. Stream 512 is split into a recycle stream 514, which is returned to crystallizer 504, and a stream 516 which is sent to a second (cold) crystallization stage 518 operated with an outlet temperature of about −65° C. to −95° C. If the slurry in crystallization stage 504 does not need dilution, the flowrate of stream 514 is zero.

Slurry 520 from crystallizer 518 is fed to a second (cold) centrifuge 522 which separates a meta-xylene crystal stream 524 from a mother liquor stream 526. A portion 528 of stream 526 may be recycled to crystallizer 518, and another portion 530 is passed through a heat exchanger 532 and removed from the meta-xylene crystallization system as net filtrate 534. At least a portion of net filtrate 534 is fed as net mother liquor stream 112 (FIG. 1), 212 (FIG. 2), 312 (FIG. 3) or 412 (FIG. 4) to the process isomerization step. Crystal stream 524 is fed to crystallizer 504 together with streams 503, 554, and optionally 514.

Slurry stream 540 from slurry drum 511 is then fed to wash column system 542 as a final product separator. Wash column system 542, which includes a melter, provides a countercurrent flow such that meta-xylene crystals are washed with liquid meta-xylene to remove crystal impurities and to attain the desired 99+percent product purity. Purified meta-xylene crystals are withdrawn as product stream 544 from the wash column system, passed through heat exchanger 502 to cool the feed, and the desired product is a liquid stream 546 of purified meta-xylene. Liquid stream 550 is recovered from the wash column system 542. A portion of stream 550 is recycled as stream 552 through a heat exchanger (not shown) or similar warming means to slurry drum 511, while another portion 554 of stream 550 is mixed with feedstream 503 going to crystallization stage 504.

In the FIG. 5 embodiment, multiple warm and cold stage crystallizers may be operated in parallel or in series in each crystallization stage to accommodate particular processing volumes. A key aspect of this invention is to process the meta-xylene feed in such a way as to deliver relatively large and relatively warm meta-xylene crystals in a slurry to the final product separator. It has been found that promoting the growth of larger crystals during the purification process both reduces material handling requirements and promotes higher product purity. With smaller crystals, the relatively larger crystal surface area makes it more difficult to separate crystals from mother liquor. Moreover, a "ripening" phenomenon has been found to lead to the growth of larger, purer crystals and melting of smaller, less pure crystals under appropriate process conditions. For relatively small temperature drops within the crystallization stages requiring multiple crystallizers because of large cooling requirements, the crystallizers may be used in parallel to reduce handling of the developing crystals and to reduce pumping requirements. For larger temperature drops, however, it is preferred to put multiple crystallizers in series at gradually decreasing temperatures to reduce temperatures shocks that could precipitate the formation of small particles rather than to promote the preferred formation of larger crystals.

Figure 8:
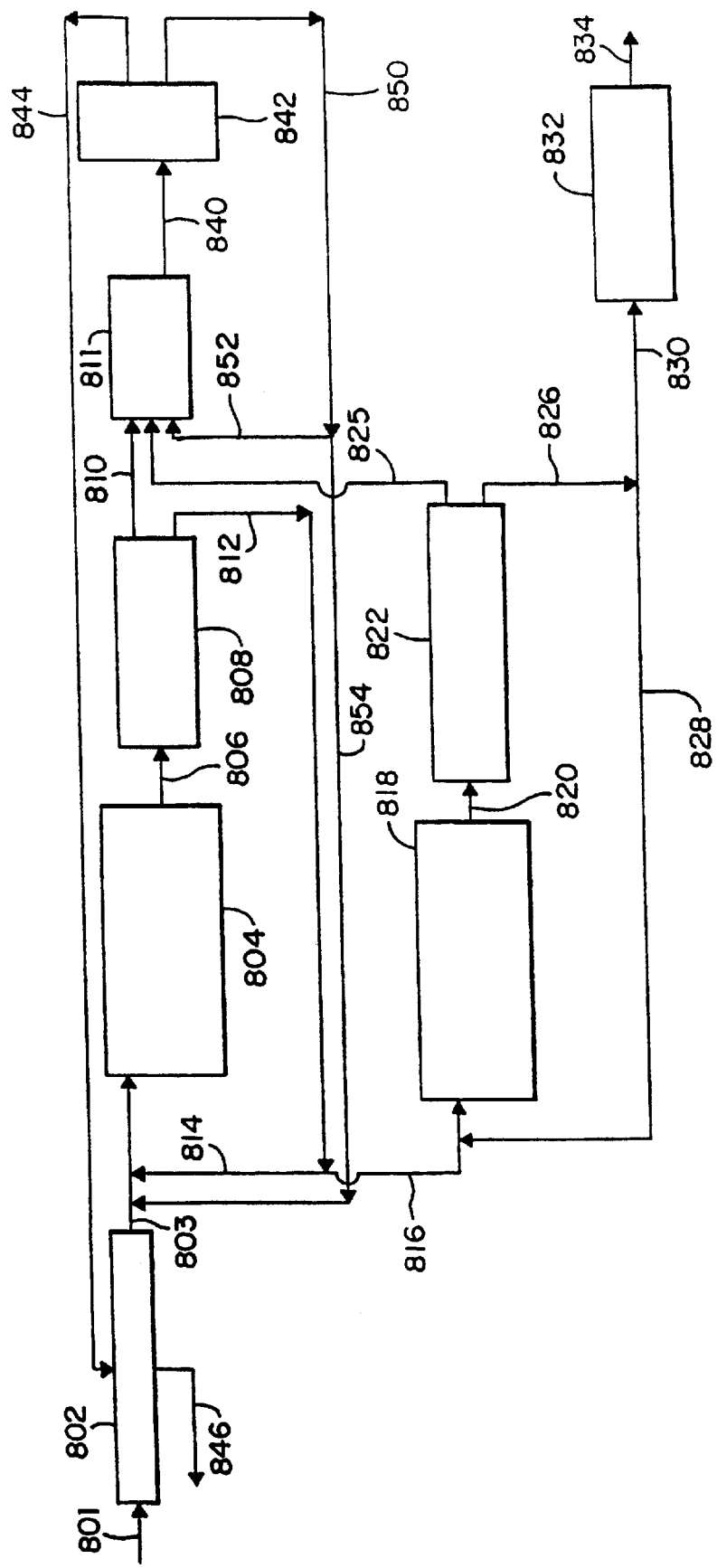
FIG. 8 is a process flow diagram illustrating an embodiment of the meta-xylene crystallization process of this invention wherein purified meta-xylene is produced by a two-stage crystallization process similar to that in FIG. 5 except the cold-stage crystals are fed to the slurry drum instead of the warm stage.

FIG. 8 is a schematic of a meta-xylene crystallization process according to the present invention in which the meta-xylene-rich residual stream is cooled against meta-xylene product from the final product separator. The residual steam feed is then combined with recycled filtrate from the wash column and optionally recycled filtrate from the warm centrifuge. Filtrate is recycled from the warm centrifuge to control the crystal concentrations in the warm crystallization stage. The combined stream is fed to the warm crystallization stage.

Referring now specifically to FIG. 8, FIG. 8 illustrates an alternative embodiment of this invention similar to FIG. 5 in which the generally corresponding apparatus components and product flow streams bear corresponding reference numerals but utilizing a "800+" numbering series respectively in place of the "500+" numbering series utilized for FIG. 5. Thus, heat exchanger 802 corresponds to heat exchanger 502, and so forth. The principal difference between FIGS. 5 and 8 is the routing of the crystals from the cold-stage centrifuge.

In this embodiment of the invention, the warm crystallization stage cools the feed stream and forms crystals. The resulting slurry 806 is then fed to the warm centrifuge 808. Part 814 of the centrifuge filtrate may be recycled to the warm crystallization stage, as previously described, while the remaining filtrate 816 becomes the feed to the cold crystallization stage. The crystals 810 from the warm centrifuge drop into a slurry drum 811. In the slurry drum, the crystals from the warm centrifuge are mixed with heated recycled filtrate 852 from the wash column. The amount of filtrate recycled is set to control the concentration of crystals leaving the slurry drum.

From the slurry drum, the slurry stream 840 is pumped to the wash column. In the wash column, the crystals are separated from the filtrate and washed of impurities. The filtrate 850 is recycled, with a portion 852 passing through a heat exchanger (not shown) and then going to the slurry drum and the rest 854 being sent to the warm crystallization stage. The crystals from the wash column are melted in the melter that is part of the wash column system, heated against the feed, and pumped to storage as the purified meta-xylene product 846.

The net filtrate 816 from the warm centrifuge is combined as needed with recycled filtrate 828 from the cold centrifuge and fed to the cold crystallization stage, where cooling and crystallization occur. The slurry 820 from the cold crystallization stage goes to the cold centrifuge 822. Part 828 of the filtrate from the cold centrifuge may be recycled to the cold crystallization stage for crystal concentration control. The remaining filtrate is warmed up in a heat exchanger 832 and removed from the meta-xylene crystallization system as net filtrate 834. At least a portion of net filtrate 834 is fed as net mother liquor stream 112 (FIG. 1), 212 (FIG. 2), 312 (FIG. 3) or 412 (FIG. 4) to the process isomerization step.

Figure 6:
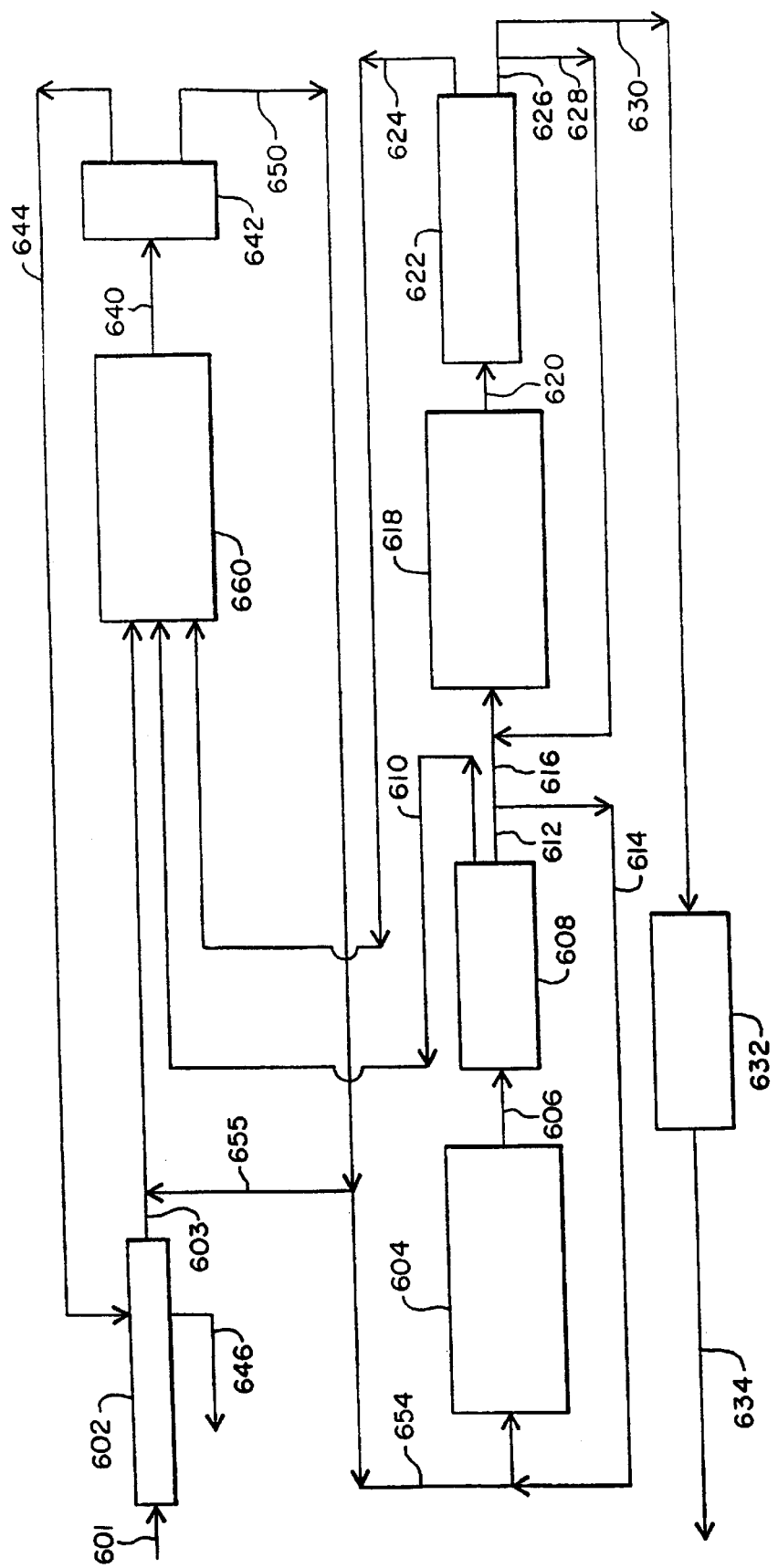
FIG. 6 is a process flow diagram illustrating an embodiment of the meta-xylene crystallization process of this invention wherein purified meta-xylene is produced by a three-stage crystallization process where the final product separator feed section comprises a hot crystallization stage. The separated crystals from the other two stages are fed to the hot stage.

FIG. 6 is a schematic of a meta-xylene crystallization process according to the present invention in which the meta-xylene-rich residual stream is cooled against the meta-xylene product from the final product separator. The cooled fresh feed is then mixed with the crystals from the warm and cold centrifuges and recycled filtrate from the wash column and fed to the hot crystallization stage. The amount of recycled filtrate is set to control the crystal concentration in the hot crystallization stage.

Referring now specifically to FIG. 6, FIG. 6 illustrates an alternative embodiment of this invention somewhat similar to FIG. 8 in which the generally corresponding apparatus components and product flow streams bear corresponding reference numerals but utilizing a "600+" numbering series respectively in place of the "800+" series used for FIG. 8. Similar to the FIG. 8 embodiment, in FIG. 6 cold-stage crystal cake coming from cold-stage centrifuge 622 are not processed in an expensive second centrifuge operation, as in FIG. 5. In place of slurry drum 811, however, the FIG. 6 embodiment utilizes a third (hot) crystallization stage 660 operated with an outlet temperature in the range of −55° C. to −68° C. In this embodiment, crystals from the warm-stage centrifuge 608, represented by flow stream 610, as well as crystals from the cold-stage centrifuge 622, represented by flow stream 624, are directed to the hot crystallization stage 660 along with cooled incoming feed stream 603. Slurry 640 from crystallizer 660, typically comprising about 35 percent solids, goes to wash column system 642. A portion 655 of liquid stream 650 from the bottom of the wash column may be recycled into feed stream 603, while the remaining portion 654 is sent to warm crystallizer 604.

The embodiment of FIG. 6 is particularly efficient for relatively large scale plants processing sufficient amounts of relatively pure meta-xylene feed to justify the higher fixed costs of three crystallization stages, each of which may comprise multiple crystallizers. Relatively pure meta-xylene refers here to meta-xylene of at least about 60 percent purity. With crystallization being carried out at three temperatures, temperature changes for the developing crystals can be carried out more gradually thereby facilitating the growth of larger crystals at warmer temperatures and thereby also minimizing refrigeration costs.

The crystal slurry stream 640 from the hot crystallization stage is sent directly to the wash column for purification. In the wash column, the filtrate is separated from the crystals. The filtrate is recycled, with a portion possibly going to the hot crystallization stage and the rest being sent to the warm crystallization stage. The crystals from the wash column are melted in the wash column system, heated against the fresh feed, and pumped to storage as the meta-xylene product 646.

The filtrate 654 from the wash column is mixed with recycled filtrate 614 from the warm centrifuge and fed to the warm crystallization stage 604. The slurry produced in the warm crystallization stage is fed to the warm centrifuge 608. The crystals 610 from the warm centrifuge are sent to the hot crystallization stage. Part 614 of the warm stage filtrate may be recycled to the warm crystallization stage for crystal concentration control, while the remaining filtrate 616 is fed to the cold crystallization stage.

Part 616 of the filtrate from the warm centrifuge may be mixed with a portion 628 of the filtrate from the cold centrifuge prior to being fed to the cold crystallization stage 618. The crystal slurry stream 620 from the cold crystallization stage goes to the cold centrifuge 622. The crystals 624 from the cold centrifuge are sent to the hot crystallization stage. The non-recycled part 630 of the filtrate is warmed up in a heat exchanger 632 and removed from the meta-xylene crystallization system as net filtrate 634. At least a portion of net filtrate 634 is fed as net mother liquor stream 112 (FIG. 1), 212 (FIG. 2), 312 (FIG. 3) or 412 (FIG. 4) to the process isomerization step.

Figure 10:
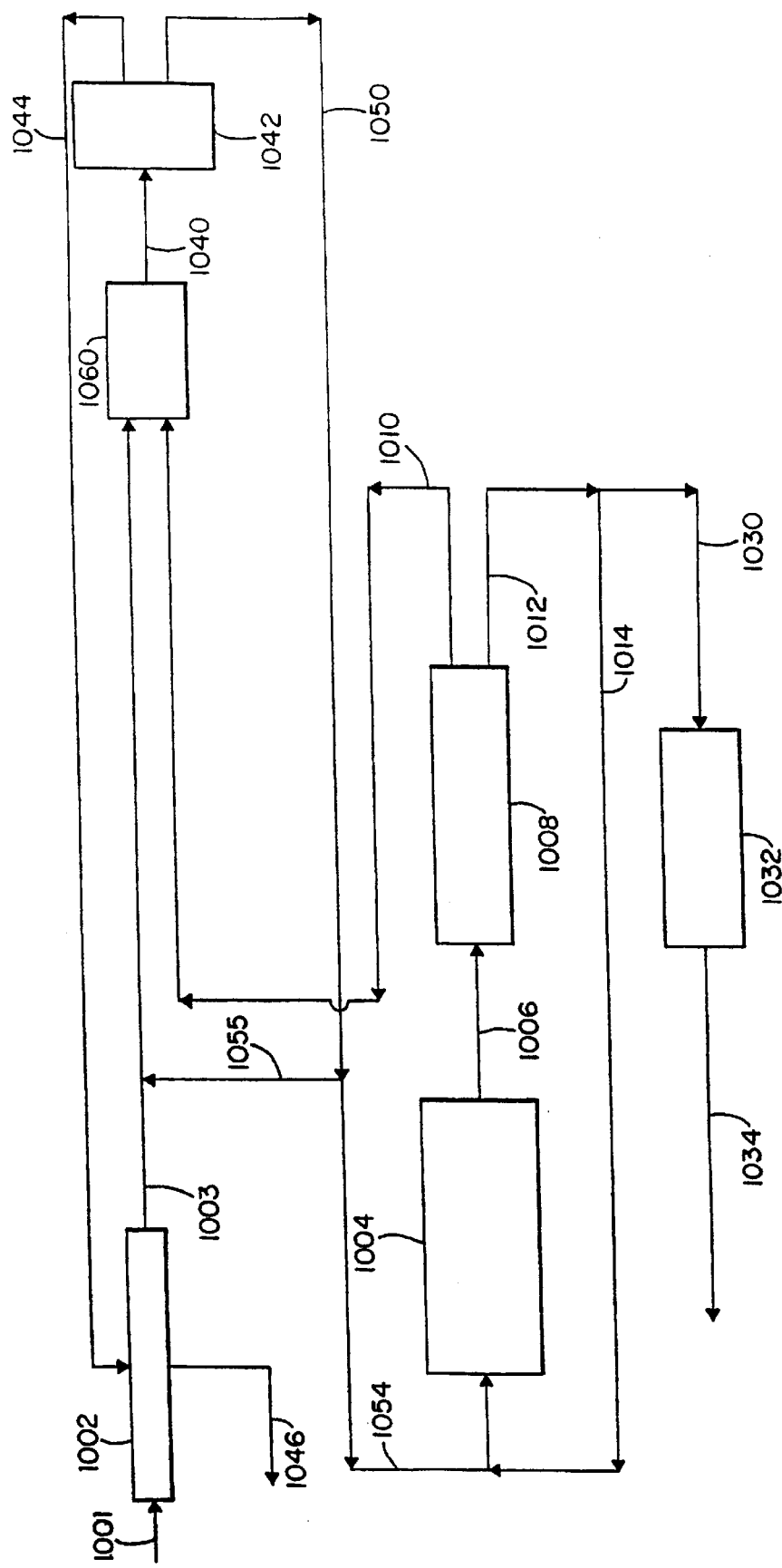
FIG. 10 is a process flow diagram illustrating an embodiment of the meta-xylene crystallization process of this invention wherein purified meta-xylene is produced by a two-stage crystallization process similar to that in FIG. 6 except the cold crystallization stage and cold-stage separator have been deleted.

FIG. 10 is a schematic of a meta-xylene crystallization according to the present invention which is the same as the embodiment in FIG. 6 except that the cold crystallization stage has been deleted. The meta-xylene feed is cooled against the meta-xylene product from the final product separator. The meta-xylene feed is then mixed with the crystals from the warm centrifuge and possibly with recycled filtrate from the wash column and is fed to the hot crystallization stage. The amount of recycled filtrate is set to control the crystal concentration in the hot crystallization stage.

Referring now specifically to FIG. 10, FIG. 10 illustrates an alternative embodiment of this invention somewhat comparable to FIG. 6 in which the generally corresponding apparatus components and product flow streams bear corresponding reference numerals but utilizing a "1000+" numbering series respectively in place of the "600+" series used for FIG. 6. The principal difference between the FIG. 10 and FIG. 6 embodiments is that FIG. 10 is optimized for lower throughputs. Part of the mother liquor 1012 from warm centrifuge 1008 may be recycled as stream 1014 and another part is sent as stream 1030 to heat exchanger 1032 and then removed from the meta-xylene crystallization system as net filtrate 1034. At least a portion of net filtrate 1034 is fed as net mother liquor stream 112 (FIG. 1). 212 (FIG. 2), 312 (FIG. 3) or 412 (FIG. 4) to the process isomerization step.

The crystal slurry stream 1040 from the hot crystallization stage 1060 is sent directly to the wash column system 1042 for purification. In the wash column, the filtrate is separated from the crystals. The filtrate is recycled, with a portion 1055 possibly going to the hot crystallization stage 1060 and the rest 1054 being sent to the warm crystallization stage 1004. The crystals from the wash column are melted in the wash column system, heated against the meta-xylene feed, and pumped to storage as the meta-xylene product 1046.

Part 1054 of the filtrate from the wash column is possibly mixed with recycled filtrate 1014 from the warm centrifuge 1008 and fed to the warm crystallization stage 1004. The slurry 1006 produced in the warm crystallization stage is fed to the warm centrifuge. The crystals 1010 from the warm centrifuge are sent to the hot crystallization stage. Part 1014 of the warm stage filtrate is recycled to the warm crystallization stage if needed for crystal concentration control.

Figure 7:
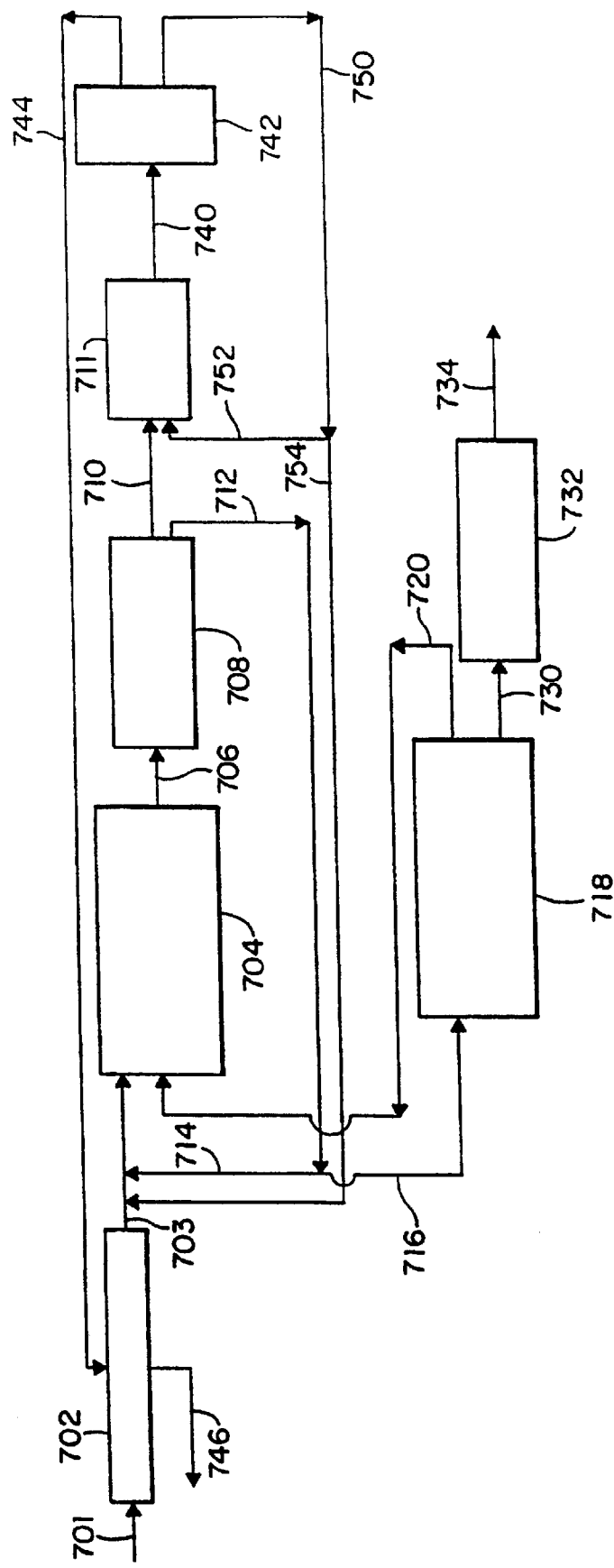
FIG. 7 is a process flow diagram illustrating an embodiment of the meta-xylene crystallization process of this invention wherein purified meta-xylene is produced by a two-stage crystallization process similar to that in FIG. 5 except there is no cold separator and the cold-stage crystal product is a slurry instead of a cake.

FIG. 7 is a schematic of a meta-xylene crystallization according to the present invention in which the meta-xylene feed is cooled against meta-xylene product from the final product separator. The meta-xylene feed is then combined with recycled filtrate from the wash column and optionally with recycled filtrate from the warm centrifuge. The filtrate recycled from the warm centrifuge is used to control the crystal concentrations in the warm crystallization stage. The combined stream is fed with crystal slurry from the cold crystallization stage.

Referring now specifically to FIG. 7, FIG. 7 illustrates an alternative embodiment of this invention similar to FIG. 5 in which the generally corresponding apparatus components and product flow streams bear corresponding reference numerals but utilizing a "700+" numbering series respectively in place of the "500+" numbering series utilized for FIG. 5. The principal difference between the FIG. 7 and FIG. 5 embodiments is that FIG. 7 is the elimination of the cold-stage centrifuge. Thus, slurry 720 from cold crystallization stage 718 is directed to warm crystallization stage 704 for further processing. The result is some relatively minor inefficiency because extra liquid that otherwise would have been removed in the cold centrifuge instead remains with the crystals and has to be moved around, and the warm crystallization stage must operate colder. However, for some designs, the inefficiency is counterbalanced by the capital savings associated with a centrifuge operation as found in FIGS. 5 and 8.

The warm crystallization stage 704 cools its combined feeds and increases the crystal concentration. The resulting slurry 706 is then fed to the warm centrifuge 708. Part 714 of the centrifuge filtrate is possibly recycled to the warm crystallization stage as previously mentioned, while the remaining filtrate 716 becomes the feed to the cold crystallization stage 718. The crystals 710 from the warm centrifuge 708 drop into a slurry drum 711. In this slurry drum, the crystals from the warm centrifuge are mixed with heated recycle filtrate 752, heated for example with a heat exchanger or similar means, from the wash column. The amount of filtrate recycled is set to control the concentration of crystals leaving the slurry drum.

From the slurry drum, the slurry stream 740 is pumped to the wash column. In the wash column, the filtrate is removed from the bottom, while the crystals are separated from the filtrate and washed of impurities. The filtrate is recycled, with a portion 752 going to the slurry drum and the rest 754 being sent to the warm crystallization stage 704. The crystals from the wash column are melted in the wash column system and drawn off to form the meta-xylene product 744. The product stream from the wash column system is heated against the fresh feed and pumped to storage as product stream 746.

Part 716 of the filtrate from the warm centrifuge is fed to the cold crystallization stage 718, where cooling and crystallization occur. The slurry 720 from the cold crystallization stage is sent to the warm crystallization stage. The net filtrate 730 is decanted off a vessel in the cold crystallization stage, warmed up in a heat exchanger 732, and removed from the meta-xylene crystallization system as net filtrate 734. At least a portion of net filtrate 734 is fed as net mother liquor stream 112 (FIG. 1), 212 (FIG. 2), 312 (FIG. 3) or 412 (FIG. 4) to the process isomerization step.

In a variation of this embodiment of the invention suitable for certain process parameters, the warm-stage crystalliquid separator 708 and slurry drum 711 may be eliminated, and slurry from warm crystallizer 704 fed directly to the final product separator 742.

Figure 9:
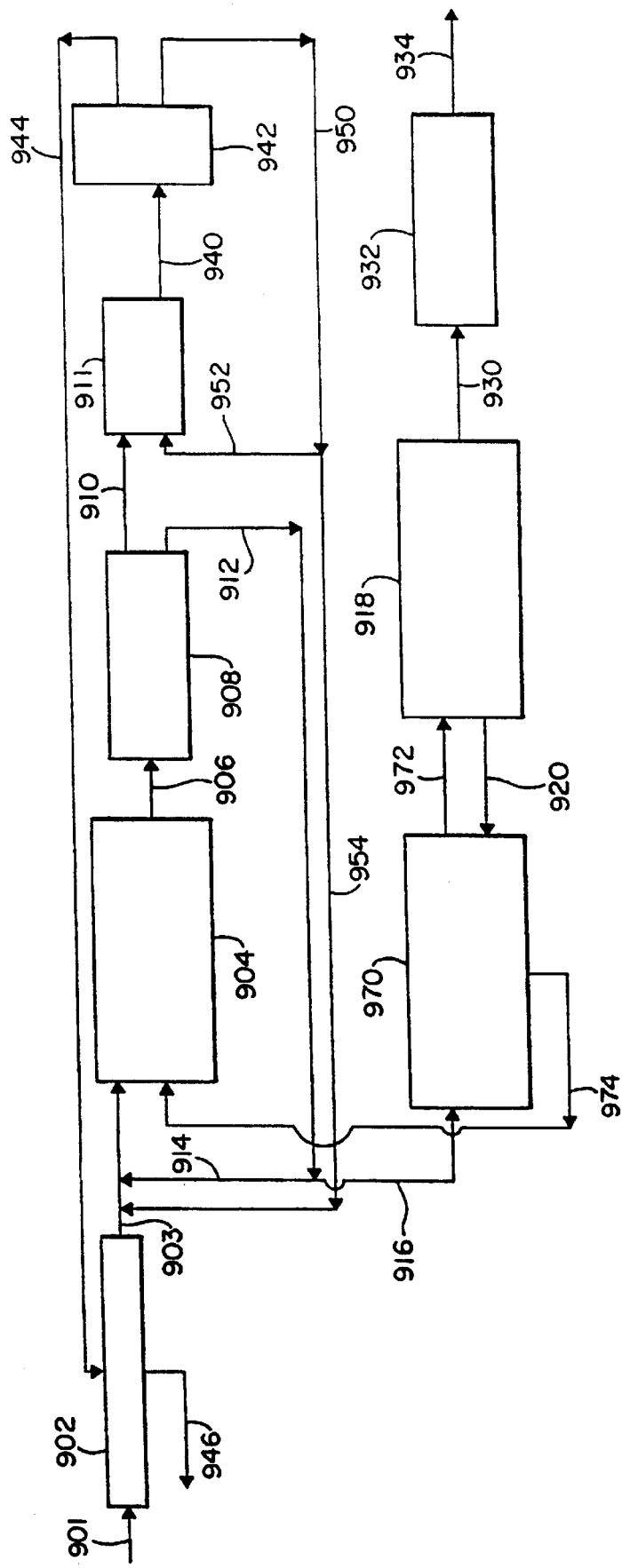
FIG. 9 is a process flow diagram illustrating an embodiment of the meta-xylene crystallization process of this invention wherein purified meta-xylene is produced by a two-stage crystallization process similar to that in FIG. 7 except a crystallizer drum has been added between the warm and cold stages.

FIG. 9 is a schematic of a meta-xylene crystallization according to the present invention which is the same as the embodiment in FIG. 7 except that a crystallizer drum has been added. In this version of the process, the meta-xylene feed is cooled against meta-xylene product from the final product separator. The meta-xylene feed is then combined with recycled filtrate from the wash column and possibly with recycled filtrate from the warm centrifuge. This combined stream is fed with crystal slurry from the cold crystallization stage by way of the crystallizer drum to the warm stage. The filtrate from the warm centrifuge is recycled to control the crystal concentrations in the warm crystallization stage.

Referring now specifically to FIG. 9, FIG. 9 illustrates an alternative embodiment of this invention similar to FIG. 7 in which the generally corresponding apparatus components and product flow streams bear corresponding reference numerals but utilizing a "900+" numbering series respectively in place of the "700+" numbering series utilized for FIG. 7. The FIG. 9 embodiment, however, provides for an additional step between the cold and warm crystallization stages to facilitate more gradual temperature increases and to spread the temperature difference between the two crystallization stages. A drum such as 970 represents lower capital and material handling costs than would another crystallizer or a centrifuge. Thus, in FIG. 9, warm centrifuge filtrate stream 916 is directed into crystallizer drum 970 which is operated at a temperature intermediate between that of the warm- and cold-stage crystallization stages. Mother liquor from drum 970 is passed as product stream 972 to cold crystallization stage 918. Slurry from crystallization stage 918 is then fed to drum 970 as product stream 920 to warm the developing crystals and to cool the liquid 916 from the warm centrifuge. The warmed slurry from drum 970 is then directed as stream 974 to the warm crystallization stage 904 for further warming and crystal growth.

The warm crystallization stage cools the feed with the recycles and increases the amount of crystals. The resulting slurry 906 is then fed to the warm centrifuge 908. Part 914 of the centrifuge filtrate is recycled to the warm crystallization stage as previously mentioned, while the remaining filtrate 916 becomes a feed to crystallizer drum 970. The crystals 910 from the warm centrifuge drop into a slurry drum 911. In this slurry drum, the crystals from the warm centrifuge are mixed with heated recycle filtrate 952, heated for example with a heat exchanger or similar means, from the wash column. The amount of filtrate recycled is set to control the concentration of crystals leaving the slurry drum.

From the slurry drum, the slurry stream 940 is pumped to the wash column. In the wash column, the filtrate is removed from the bottom, while the crystals are separated from the filtrate and washed of impurities. The filtrate is recycled, with a portion 952 going to the slurry drum and the rest 954 being sent to the warm crystallization stage 904. The crystals from the wash column are melted in the wash column system and drawn off to form the meta-xylene product 944. The product stream from the wash column system is heated against the meta-xylene feed and pumped to storage as product stream 946.

Filtrate 916 from the warm centrifuge is fed to the crystallizer drum 970 along with slurry 920 from the cold crystallization stage 918. In this drum, the filtrate is cooled and the slurry is heated. Depending on the temperatures, solids concentrations, and flowrates of the two inlet streams, there may be a small amount of melting or crystal growth in this drum. Out of the bottom of the drum, slurry 974 is sent to the warm crystallization stage. The upper section of the crystallizer drum is used to separate a liquid feed 972 for the cold crystallization stage from most of the crystals.

The purpose of the crystallizer drum 970 in this embodiment is to reduce the temperature differences between the warm crystallization stage 904 and its slurry feed 974 and between the cold crystallization stage 918 and its filtrate feed 972. The addition of the drum to the process design (FIG. 7 is the same except for the addition of this drum) can also result in a higher warm crystallization stage temperature. The smaller temperature differences and higher crystallization temperature both promote the growth of larger crystals.

The clarified liquid 972 from the top of the crystallizer drum is fed to the cold crystallization stage, where cooling and crystallization occur. The slurry 920 from the cold crystallization stage is sent to the crystallizer drum. The net filtrate 930 is decanted off a vessel in the cold crystallization stage, warmed up in a heat exchanger 932, and removed from the meta-xylene crystallization system as net filtrate 934. At least a portion of net filtrate 934 is fed as net mother liquor stream 112 (FIG. 1), 212 (FIG. 2), 312 (FIG. 3) or 412 (FIG. 4) to the process isomerization step.

In a variation of this embodiment of the invention suitable for certain process parameters, the warm-stage crystal/liquid separator 908 and slurry drum 911 may be eliminated, and slurry from warm crystallizer 904 fed directly to the final product separator 942.

In still another variation of this invention embodiment suitable for certain process parameters, the warm-stage crystal/liquid separator 908 and slurry drum 911 may be eliminated, and, in addition, the positions of warm crystallizer 904 and crystallizer drum 970 are interchanged such that feed 903 flows to crystallizer drum 970 and slurry from crystallizer drum 970 is fed directly to the final product separator 942.

Figure 11:
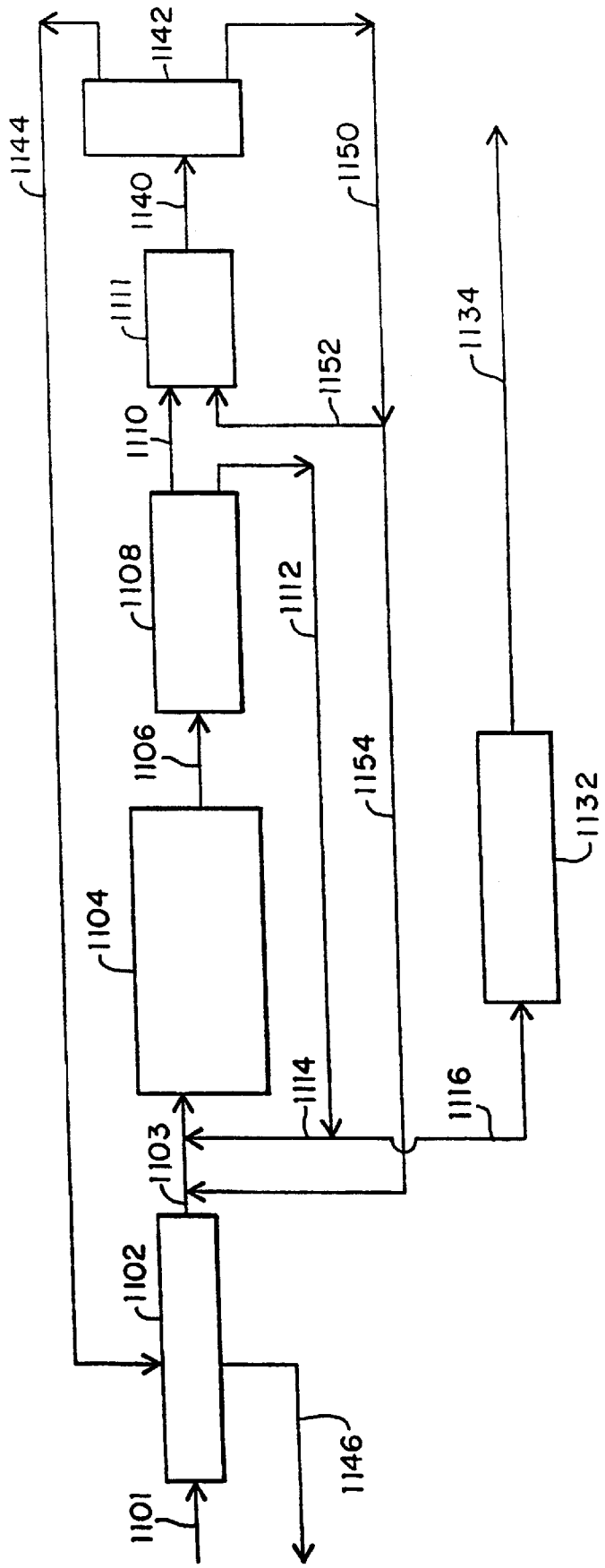
FIG. 11 is a process flow diagram illustrating still another embodiment of this invention wherein purified meta-xylene is produced by a crystallization process similar to that in FIG. 5 except the cold crystallization stage and cold-stage separator have been deleted.

Still another preferred meta-xylene crystallization system for use with the invention of FIGS. 1–4 is schematically illustrated in FIG. 11. Referring now specifically to FIG. 11, the raffinate stream 1101 (stream 108, 208, 308, or 408 respectively in FIGS. 1–4) from the Adsorption Unit is fed to one or more exchangers to cool the meta-xylene-rich stream prior to crystallization FIG. 11 shows the feed cooled in an exchanger with the heat being transferred to the meta-xylene product. It is understood that there are various possible arrangements for efficient heat integration for the cooling of the feed and heating of the crystallization unit products that can be easily devised by one practiced in the art and that the feed-product heat interchange is just one of the possible approaches to such integration.

The cooled feed 1103 then enters a crystallization stage 1104. In the crystallization stage, meta-xylene is crystallized, and crystal slurry is formed. This slurry 1106 is fed to a first separator 1108 to separate the meta-xylene crystals 1110 from the mother liquor 1112. This first separator could be a filter, a centrifuge, a wash column, or a hydrocyclone (or multiples of any type in parallel). To ensure a higher purity cake, a cooled liquid wash (not shown) could be applied as part of the separator step. Also, if the centrifuge type used has a screen drain, then this stream (not shown) would be collected and recycled to the crystallization stage. If necessary to keep the concentration of crystals low enough in the first separator feed, part of the first separator mother liquor, prior to heating, can be recycled (not shown) to the crystallizer(s).

If the crystal concentration in a slurry is too high, then there will be pluggage problems in the piping. To keep the crystal percentage low enough in the slurry feeding the first separator, a portion 1114 of the first separator mother liquor can optionally be recycled to the crystallization stage. Whatever first separator liquid is not recycled is heated and is fed as net mother liquor stream 112 (FIG. 1), 212 (FIG. 2), 312 (FIG.3), or 412 (FIG. 4) to the process isomerization step.

The crystals from the first separator are reslurried in a reslurry drum 1111. From this drum, the slurry 1140 is fed to a final product separator 1142 where the crystals 1144 are again separated from the liquid 1150. The meta-xylene is melted and heated up to storage temperature in one or more heat exchangers 1102. Part of the mother liquor from the product separator is recycled to the reslurry drum 1152, and the rest would be recycled to the crystallizers 1154. The reslurry drum would require a small amount of heat addition (not shown), which may be added by heating the recycle stream feeding the drum. This heat could be supplied, for example, by interchange with the feed.

A variation (not shown) of the above Meta-Xylene Crystallization Unit design would be to delete the reslurry drum and first separator. In this case, the crystallization stage feeds slurry directly to the final product separator.

Another variation (not shown) of the above Meta-Xylene Crystallization Unit design would be to convert the reslurry drum of FIG. 11 into a melt drum where some or all of the crystals would be melted and the resulting stream was fed to a second crystallization stage located between the drum and the final separator. This would be the two-stage version of the one-stage process in FIG. 11.

The several embodiments of the present invention all realize significant and surprising capital and operating cost savings relative to prior art processes in this field. Prior to the surprising discoveries of this invention, both the accepted teachings and standard practices in this art would have led others away from even attempting the process and apparatus configurations of this invention, leading others to believe such processes could not and would not work.

It will be apparent to those skilled in the art that other changes and modifications may be made in the above-described apparatus and processes without departing from the scope of the invention herein, and it is intended that all matter contained in the above description shall be interpreted in an illustrative and not in a limiting sense.

What is claimed is:

1. A process for integrated processing of a hydrocarbon feed stream consisting essentially of C-8+ aromatic hydrocarbons to recover a high-purity meta-xylene product in combination with efficient separation and recovery of other C-8 aromatic hydrocarbon components including para-xylene and optionally ortho-xylene, said process comprising the sequential steps of:

(a) processing the C-8+ aromatic hydrocarbon feed by means of a first splitter column, which comprises a single column or a linked series of at least two separate columns wherein a bottoms feed from an upper column feeds the top of an adjacent lower column and distillate from said lower column feeds the bottom of the adjacent upper column while operating said first splitter column so as to produce an ortho-xylene-rich stream and a first splitter distillate stream containing predominant portions of any ethylbenzene, para-xylene and meta-xylene in all of the feeds to the first splitter column, the proportion of ortho-xylene in said distillate stream being maintained at a level low enough to avoid crystallization of ortho-xylene in a downstream meta-xylene crystallization step;

(b) processing the first splitter distillate stream by means of an adsorption treatment carried out so as to separate substantially all of the para-xylene and removing desorbent to leave a meta-xylene-rich residual stream containing substantially all of the meta-xylene; and, (c) passing said meta-xylene-rich residual stream directly without intermediate fractionation to a multi-stage meta-xylene crystallization process comprising at least two crystal reformation stages including: (i) at least one meta-xylene crystallization stage operated at a temperature of about −53° C. to −95° C.; (ii) said first crystallization stage operating in conjunction with at least a second crystal reformation stage, which may comprise a second crystallization stage operated at a temperature below that of said first crystallization stage or a slurry drum operated at a temperature above that of said first crystallization stage, for processing at least a portion of the product from said first crystallization stage so as to produce an end-step slurry of meta-xylene crystals; and (iii) passing said end-step slurry of meta-xylene crystals to a final product separator to produce purified meta-xylene crystals and separator liquid; wherein each of steps (i), (ii) and (iii) is carried out with essentially no heat input to the meta-xylene crystallization process thereby to realize a minimum of net melting of crystals.

2. A process according to claim 1 wherein said meta-xylene crystallization treatment comprises the steps of:

(a) passing said meta-xylene-rich residual stream to a first crystallization stage operated with an outlet temperature of about −60° C. to −80° C. to produce a first-stage slurry which is separated into first-stage crystals and first-stage mother liquor;

(b) optionally recycling a first portion of said first-stage mother liquor to said first crystallization stage and passing a second portion of said first-stage mother liquor to a second crystallization stage operated at a temperature colder than the first crystallization stage with an outlet temperature of about −65° C. to −95° C.

to produce a second-stage slurry which is separated into second-stage crystals and second-stage mother liquor;

(c) optionally recycling a first portion of said second-stage mother liquor to said second crystallization stage, withdrawing a second portion of said second-stage mother liquor as net mother liquor steam, and passing said second-stage crystals to said first crystallization stage;

(d) passing said first-stage crystals to a slurry drum operated warmer than the first crystallization stage at a temperature of about −51° C. to −68° C. to form a drum slurry consisting of drum crystals and mother liquor;

(e) passing said drum slurry to a final product separator to produce purified meta-xylene crystals and separator liquid;

wherein each of steps (a) to (e) is carried out in conjunction with substantially no heat input to the process thereby to realize a minimum of net melting of crystals; and, (f) separating said purified crystals from said separator liquid, recycling a first portion of said separator liquid to said first crystallization stage and recycling a second portion of said separator liquid to said slurry drum, and recovering the purified meta-xylene product with a purity of 99 percent or higher.

3. A process according to claim 1 wherein said meta-xylene crystallization treatment comprises the steps of:

(a) passing said meta-xylene-rich residual stream to a first crystallization stage operated with an outlet temperature of about −60° C. to −80° C. to produce a first-stage slurry which is separated into first-stage crystals and first-stage mother liquor;

(b) optionally recycling a first portion of said first-stage mother liquor to said first crystallization stage and passing a second portion of said first-stage mother liquor to a second crystallization stage operated at a temperature colder than the first crystallization stage with an outlet temperature of about −65° C. to 95° C. to produce a second-stage slurry which is separated into second-stage crystals and second-stage mother liquor;

(c) optionally recycling a first portion of said second-stage mother liquor to said second crystallization stage and withdrawing a second portion of said second-stage mother liquor as net mother liquor stream;

(d) passing said first-stage and said second-stage crystals to a slurry drum operated warmer than the first crystallization stage at a temperature of about −51° C. to −68° C. to form a drum slurry consisting of drum crystals and mother liquor;

(e) passing said drum slurry to a final product separator to produce purified meta-xylene crystals and separator liquid;

wherein each of steps (a) to (e) is carried out in conjunction with substantially no heat input to the process thereby to realize a minimum of net melting of crystals; and, (f) separating said purified crystals from said separator liquid, recycling a first portion of said separator liquid to said first crystallization stage and recycling a second portion of said separator liquid to said slurry drum, and recovering the purified meta-xylene product with a purity of 99 percent or higher.

4. A process according to claim 1 wherein said meta-xylene crystallization treatment comprises the steps of:

(a) passing said meta-xylene-rich residual stream to a first crystallization stage operated with an outlet temperature of about −55° C. to −68° C. to produce a first-stage slurry consisting of first-stage crystals and first-stage mother liquor;

(b) passing said first-stage slurry to a final product separator to produce purified meta-xylene crystals and separator liquid;

(c) separating said purified crystals from said separator liquid, optionally recycling a first portion of said separator liquid to said first crystallization stage and passing a second portion of said separator liquid to a second crystallization stage operated at a temperature colder than the first crystallization stage with an outlet temperate of about −60° C. to −80° C. to produce a second-stage slurry which is separated into second-stage crystals and second-stage mother liquor;

(d) passing said second-stage crystals to said first crystallization stage;

(e) optionally recycling a first portion of said second-stage mother liquor to said second crystallization stage and passing a second portion of said second-stage mother liquor to a third crystallization stage operated at a temperature colder than the second crystallization stage with an outlet temperature of about −65° C. to −95° C. to produce a third-stage slurry which is separated into third-stage crystals and third-stage mother liquor;

(f) optionally recycling a first portion of said third-stage mother liquor to said third crystallization stage, withdrawing a second portion of said third-stage mother liquor as net mother liquor stream, and passing said third-stage crystals to said first crystallization stage;

wherein each of steps (a) to (f), except for said step of separating said purified crystals from said separator liquid, is carried out in conjunction with substantially no heat input to the process thereby to realize a minimum of net melting of crystals; and, (g) recovering the purified meta-xylene product with a purity of 99 percent or higher from the final product separator.

5. A process according to claim 1 wherein said meta-xylene crystallization treatment comprises the steps of:

(a) passing said meta-xylene-rich residual stream to a first crystallization stage operated with an outlet temperature of about −55° C. to −68° C. to produce a first-stage slurry consisting of meta-xylene crystals and mother liquor;

(b) passing said first-stage slurry to a final product separator to produce purified meta-xylene crystals and separator liquid;

(c) separating said purified crystals from said separator liquid, optionally recycling a first portion of said separator liquid to said first crystallization stage and passing a second portion of said separator liquid to a second crystallization stage operated at a temperature colder than the first crystallization stage with an outlet temperature of about −60° C. to −80° C. to produce a second-stage slurry which is separated into second-stage crystals and second-stage mother liquor;

(d) passing said second-stage crystals to said first crystallization stage;

(e) optionally recycling a first portion of said second-stage mother liquor to said second crystallization stage and withdrawing a second portion of said second-stage mother liquor as net mother liquor stream;

wherein each of steps (a) to (e), except for said step of separating said purified crystals from said separator liquid, is carried out in conjunction with substantially no heat input to the process thereby to realize a minimum of net melting of crystals; and, (f) recovering the purified meta-xylene product with a purity of 99 percent or higher from the final product separator.

6. A process according to claim 1 wherein said meta-xylene crystallization treatment comprises the steps of:

(a) passing said meta-xylene-rich residual stream to a first crystallization stage operated with an outlet temperature of about −60° C. to −80° C. to produce a first-stage slurry which is separated into first-stage crystals and first-stage mother liquor;

(b) optionally recycling a first portion of said first-stage mother liquor to said first crystallization stage and passing a second portion of said first-stage mother liquor to a second crystallization stage operated at a temperature colder than the first crystallization stage so as to produce a second-stage slurry, consisting of second-stage crystals and liquor, and second-stage mother liquor at a temperature of about −65° C. to −95° C.;

(c) passing said second-stage slurry to said first crystallization stage and withdrawing said second-stage mother liquor as net mother liquor stream;

(d) passing said first-stage crystals to a slurry drum operated warmer than the first crystallization stage at a temperature of about −51° C. to −68° C. to form a drum slurry consisting of drum crystals and mother liquor;

(e) passing said drum slurry to a final product separator to produce purified meta-xylene crystals and separator liquid;

wherein each of steps (a) to (e) is carried out in conjunction with substantially no heat input to the process thereby to realize a minimum of net melting of crystals; and, (f) separating said purified crystals from said separator liquid, recycling a first portion of said separator liquid to said first crystallization stage and recycling a second portion of said separator liquid to said slurry drum, and recovering the purified meta-xylene product with a purity of 99 percent or higher.

7. A process according to claim 1 wherein said meta-xylene crystallization treatment comprises the steps of:

(a) passing said meta-xylene-rich residual stream to a first crystallization stage operated with an outlet temperature of about −60° C. to −80° C. to produce a first-stage slurry which is separated into first-stage crystals and first-stage mother liquor;

(b) optionally recycling a first portion of said first-stage mother liquor to said first crystallization stage and passing a second portion of said first-stage mother liquor to a crystallizer drum operated colder than the first crystallization stage at a temperature of about −60° C. to −95° C. to produce a crystallizer drum slurry, consisting of crystallizer drum crystals and liquor and crystallizer drum mother liquor;

(c) recycling said crystallizer drum slurry to said first crystallization stage and passing said crystallizer drum mother liquor to a second crystallization stage operated at a temperature colder than the crystallizer drum so as to produce a second-stage slurry, consisting of second-stage crystals and liquor, and second-stage mother liquor at a temperature of about −70° C. to −95° C.;

(d) recycling said second-stage slurry to said crystallizer drum and withdrawing said second-stage mother liquor as net mother liquor stream;

(e) passing said first-stage crystals to a slurry drum operated warmer than the first crystallization stage at a temperature of about −51° C. to −68° C. to form a slurry drum slurry consisting of slurry drum crystals and slurry drum mother liquor;

(f) passing said slurry drum slurry to a final product separator to produce purified meta-xylene crystals and separator liquid;

wherein each of steps (a) to (f) is carried out in conjunction with substantially no heat input to the process thereby to realize a minimum of net melting of crystals; and, (g) separating said purified crystals from said separator liquid, recycling a first portion of said separator liquid to said first crystallization stage and recycling a second portion of said separator liquid to said slurry drum, and recovering the purified meta-xylene product with a purity of 99 percent or higher.

8. A process according to claim 1 wherein said meta-xylene crystallization treatment comprises the steps of:

(a) passing said meta-xylene-rich residual stream to a first crystallization stage operated with an outlet temperature of about −53° C. to −68° C. to produce a first-stage slurry consisting of first-stage crystals and first-stage mother liquor;

(b) passing said first-stage slurry to a final product separator to produce purified meta-xylene crystals and separator liquid;

(c) separating said purified crystals from said separator liquid, and recovering the purified meta-xylene product with a purity of 99 percent or higher;

(d) optionally recycling a first portion of said separator liquid to said first crystallization stage and passing a second portion of said separator liquid to a second crystallization stage operated at a temperature colder than said first crystallization stage so as to produce second-stage slurry, consisting of second-stage crystals and liquor, and second-stage mother liquor at a temperature of about −55° C. to −95° C.; and, (e) passing said second-stage slurry to said first crystallization stage and withdrawing said second-stage mother liquor as net mother liquor stream;

wherein each of steps (a), (b), (d) and (e) is carried out in conjunction with substantially no heat input to the process thereby to realize a minimum of net melting of crystals.

9. A process according to claim 1 wherein said meta-xylene crystallization treatment comprises the steps of:

(a) passing said meta-xylene-rich residual stream to a first crystallization stage operated with an outlet temperature of about −53° C. to −68° C. to produce a first-stage slurry consisting of first-stage crystals and first-stage mother liquor;

(b) passing said first-stage slurry to final product separator to produce purified meta-xylene crystals and separator liquid;

(c) separating said purified crystals from said separator liquid and recovering the purified meta-xylene product with a purity of 99 percent or higher;

(d) recycling a first portion of said separator liquid to said first crystallization stage and/or recycling a second portion of said separator liquid to a crystallizer drum operated colder than the first crystallization stage at a temperature of about −55° C. to −85° C. to produce a drum slurry, consisting of drum crystals and liquor, and drum mother liquor;

(e) recycling said drum slurry to said first crystallization stage and passing said drum mother liquor to a second crystallization stage operated colder than the crystallizer drum so as to produce second-stage slurry, consisting of second-stage crystals and liquor, and second-stage mother liquor at a temperature of about −60° C. to −95° C.; and, (f) recycling said second-stage slurry to said crystallizer drum and withdrawing said second-stage mother liquor as net mother liquor stream;

wherein each of steps (a), (b), (d), (e) and (f) is carried out in conjunction with substantially no heat input to the process thereby to realize a minimum of net melting of crystals.

10. A process according to claim 1 wherein said meta-xylene crystallization treatment comprises the steps of:

(a) passing said meta-xylene-rich residual stream with one or two other streams to a crystallizer drum operated at a temperature of about −53° C. to −68° C. to produce a drum slurry, consisting of drum crystals and liquor, and a drum mother liquor;

(b) passing said drum slurry to a final product separator to separate purified meta-xylene crystals and a separator liquid, and recovering the purified meta-xylene product with a purity of 99 percent or higher from the final product separator;

(c) recycling said drum mother liquor to a first crystallization stage operated colder than the crystallizer drum so as to produce a first-stage slurry, consisting of first-stage crystals and liquor, and a first-stage mother liquor at a temperature of about −55° C. to −85° C.;

(d) recycling said separator liquid to the first crystallizer stage and/or to the crystallizer drum;

(e) passing said first-stage slurry to the crystallizer drum;

(f) passing said first-stage mother liquor to a second crystallization stage operated at a temperature colder than the first crystallization stage so as to produce a second-stage slurry, consisting of second-stage crystals and liquor, and a second-stage mother liquor at a temperature of about −60° C. to −95° C.; and, (g) recycling said second stage slurry to the first crystallization stage and withdrawing said second-stage mother liquor as net mother liquor stream;

wherein each of steps (a) to (g), except for said step of recovering the purified meta-xylene product from the final product separator, is carried out in conjunction with substantially no heat input to the process thereby to realize a minimum of net melting of crystals.

11. A process according to claim 1 wherein said meta-xylene crystallization treatment comprises the steps of:

(a) passing said meta-xylene-rich residual stream to a crystallization stage operated with an outlet temperature of about −60° C. to −95° C. to produce a crystallizer slurry which is separated into crystallizer meta-xylene crystals and crystallizer mother liquor;

(b) withdrawing a first portion of said crystallizer mother liquor as net mother liquor stream, optionally recycling a second portion of said crystallizer mother liquor to said crystallization stage, and passing said crystallizer crystals to a slurry drum operating warmer than the crystallization stage at a temperature of about −51° C. to −68° C. to form a drum slurry consisting of drum crystals and drum mother liquor;

(c) passing said drum slurry to a final product separator to produce purified meta-xylene crystals and separator liquid;

wherein each of steps (a), (b), and (c) is carried out with substantially no heat input to the process thereby to minimize refrigeration usage;

(d) separating said purified crystals from said separator liquid; recycling a first portion of said separator liquid to said crystallization stage and recycling a second portion of said separator liquid to said slurry drum, and recovering the purified meta-xylene product with a purity of 99 percent or higher.

12. A process according to claim 1 wherein said multi-stage meta-xylene crystallization treatment comprises a first meta-xylene crystallization stage operated at a temperature of about −53° C. to −95° C., said first crystallization stage operating in conjunction with a second crystallization stage operated at a temperature below that of said first crystallization stage, and further comprising a third crystal reformation stage, which comprises a third crystallization stage operated at a temperature below that of said second crystallization stage or a slurry drum operating in conjunction with said first and second crystallization stages at a temperature above that of said first crystallization stage.

13. A process according to any of claims 1–12 further comprising the steps of processing the net mother liquor stream by means of an isomerization treatment operated so as to approach thermodynamic equilibrium among the remaining xylene components in an isomerization outlet stream, fractionating off light components that would interfere with the downstream operations, and recycling said isomerization outlet stream to said first splitter column.

14. A process according to claim 13 further comprising the step of passing at least a portion of said ortho-xylene-rich stream to said isomerization treatment.

15. A process according to claim 13 further comprising the steps of: passing at least a portion of said ortho-xylene-rich stream to an ortho-xylene recovery column operated to produce a concentrated ortho-xylene distillate stream and a bottoms stream comprising C-9+ aromatic hydrocarbons; optionally recovering at least a portion of said concentrated ortho-xylene distillate stream as purified ortho-xylene product and recycling the remaining portion to said isomerization treatment or, alternately, recycling all of said concentrated ortho-xylene distillate stream to said isomerization treatment.

16. A process according to claim 13 further comprising the steps of: withdrawing said ortho-xylene-rich stream as a side stream from a lower portion of said first splitter column, passing said side stream to said isomerization treatment, and withdrawing a first splitter bottoms stream containing C-9+ aromatic hydrocarbons and optionally ortho-xylene.

17. A process according to claim 16 further comprising the steps of passing another portion of said first splitter bottoms stream to an ortho-xylene product column operated to produce a concentrated ortho-xylene distillate stream for recovery as purified ortho-xylene product and a bottoms stream comprising C-9+ aromatic hydrocarbons.

18. A process according to claim 13 further comprising the steps of: passing said ortho-xylene-rich stream, which is the first splitter bottoms stream in this case, to a second splitter column operated so as to produce a second splitter distillate stream consisting essentially of ortho-xylene and a first, lighter fraction of the C-9+ aromatic hydrocarbons present in said ortho-xylene-rich stream, and a second splitter bottom stream comprising a second, heavier fraction of the C-9+ aromatic hydrocarbons present in said ortho-xylene-rich stream; passing said second splitter distillate stream as a first feed stream to a disproportionation treatment operated so as to at least partially convert said feed stream to a mixture of para-xylene, meta-xylene, benzene, and possibly ortho-xylene; separating a stream of xylene and heavier components of said mixture from the lighter components including benzene; and, recycling said stream of xylene and heavier components to said first stripper column.

19. A process according to claim 18 further comprising the step of introducing toluene as a second feed stream to said disproportionation treatment together with said second splitter distillate stream.

20. A process according to claim 13 further comprising the steps of: passing said ortho-xylene-rich stream, which in this case is the first splitter bottoms stream, to an ortho-xylene product column operated to produce a concentrated ortho-xylene distillate stream for recovery as purified ortho-xylene product and a bottoms stream consisting essentially of ortho-xylene and C-9+ aromatic hydrocarbons; passing said bottoms stream to a second splitter column operated so as to produce a second splitter distillate stream consisting essentially of ortho-xylene and a first, lighter fraction of said C-9+ aromatic hydrocarbons, and a second splitter bottoms stream comprising a second, heaver fraction of the C-9+ aromatic hydrocarbons; passing said second splitter distillate stream as a first feed stream to a disproportionation treatment operated so as to at least partially convert said feed stream to a mixture of para-xylene, meta-xylene, benzene, and possibly ortho-xylene; separating a stream of xylene and heavier components of said mixture from the lighter components including benzene; and, recycling said stream of xylene and heaver components to said first stripper column.

21. A process according to claim 20 further comprising the step of introducing toluene as a second feed stream to said disproportionation treatment together with said second splitter distillate stream.

* * * * *